(12) United States Patent
Bisso et al.

(10) Patent No.: US 9,528,145 B2
(45) Date of Patent: *Dec. 27, 2016

(54) RARE EARTH SPATIAL/SPECTRAL BARCODES FOR MULTIPLEXED BIOCHEMICAL TESTING

(71) Applicant: Massachusetts Institute of Technology, Cambridge, MA (US)

(72) Inventors: Paul Bisso, Belmont, MA (US); Albert Swiston, Baltimore, MD (US); Jiseok Lee, Melrose, MA (US); Patrick S. Doyle, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 197 days.

This patent is subject to a terminal disclaimer.

(21) Appl. No.: 14/214,594

(22) Filed: Mar. 14, 2014

(65) Prior Publication Data

US 2014/0273255 A1     Sep. 18, 2014

Related U.S. Application Data

(60) Provisional application No. 61/800,995, filed on Mar. 15, 2013, provisional application No. 61/801,351, filed on Mar. 15, 2013.

(51) Int. Cl.
*G01N 21/64* (2006.01)
*C12Q 1/68* (2006.01)
(Continued)

(52) U.S. Cl.
CPC ......... *C12Q 1/6825* (2013.01); *C09K 11/7773* (2013.01); *G07D 7/0026* (2013.01);
(Continued)

(58) Field of Classification Search
CPC ... C09K 11/7766; C09K 11/7773; C12Q 1/68; C12Q 1/6825; Y10T 436/13; Y10T 436/143333; Y10T 436/25; G01N 21/64; G01N 21/6456; G01N 21/6486
(Continued)

(56) References Cited

U.S. PATENT DOCUMENTS

| 5,674,698 A | 10/1997 | Zarling et al. |
| 5,698,397 A | 12/1997 | Zarling et al. |

(Continued)

FOREIGN PATENT DOCUMENTS

| CA | 2125228 A1 | 12/1994 |
| WO | 2010107720 A2 | 9/2010 |
| WO | 2011156434 A2 | 12/2011 |

OTHER PUBLICATIONS

Yan et al. Journal of the American Chemical Society, vol. 134, Sep. 26, 2012, pp. 16558-16561.*

(Continued)

*Primary Examiner* — Maureen Wallenhorst
(74) *Attorney, Agent, or Firm* — McCarter & English, LLP; David R. Burns

(57) ABSTRACT

Hydrogel microparticles spatially and spectrally encoded using upconverting phosphor nanoparticles are described for use in biochemical testing. In each microparticle, upconversion nanocrystals having spectrally distinguishable emission spectra are disposed in different pardons of an encoding region of the microparticle.

28 Claims, 33 Drawing Sheets
(10 of 33 Drawing Sheet(s) Filed in Color)

(51) Int. Cl.
  *C09K 11/77* (2006.01)
  *G07D 7/00* (2016.01)
  *G07D 7/12* (2016.01)
  *G07D 7/20* (2016.01)
(52) U.S. Cl.
  CPC ............ *G07D 7/122* (2013.01); *G07D 7/2033* (2013.01); *G01N 21/6486* (2013.01); *Y10T 436/13* (2015.01); *Y10T 436/143333* (2015.01)
(58) Field of Classification Search
  USPC ..... 436/56, 82, 94, 164, 165, 166, 172, 174, 436/501, 523; 422/82.05, 82.08, 52
  See application file for complete search history.

(56) References Cited

U.S. PATENT DOCUMENTS

| | | | |
|---|---|---|---|
| 7,874,489 | B2 | 1/2011 | Mercolino |
| 7,947,487 | B2* | 5/2011 | Doyle .............. G01N 33/54313 422/68.1 |
| 8,220,716 | B2 | 7/2012 | Mercolino |
| 8,247,018 | B2 | 8/2012 | Mercolino |
| 8,458,475 | B2 | 6/2013 | Mercolino |
| 9,053,364 | B2 | 6/2015 | Mercolino et al. |
| 2006/0269483 | A1 | 11/2006 | Austin et al. |
| 2010/0041017 | A1 | 2/2010 | Tsukada et al. |
| 2010/0172898 | A1 | 7/2010 | Doyle et al. |
| 2010/0261263 | A1 | 10/2010 | Vo-Dinh et al. |
| 2011/0127445 | A1 | 6/2011 | Zhang et al. |
| 2011/0189777 | A1 | 8/2011 | Graziano et al. |
| 2011/0263747 | A1 | 10/2011 | Doyle et al. |
| 2011/0306065 | A1* | 12/2011 | Friedberg .............. B82Y 15/00 435/7.25 |
| 2012/0003755 | A1* | 1/2012 | Chapin ............. B01L 3/502761 436/501 |
| 2012/0107820 | A1 | 5/2012 | Pregibon et al. |
| 2012/0273564 | A1 | 11/2012 | Mercolino et al. |
| 2012/0280144 | A1 | 11/2012 | Guilfoyle et al. |
| 2013/0193346 | A1 | 8/2013 | Justel et al. |
| 2013/0244894 | A1 | 9/2013 | Mercolino |
| 2013/0273559 | A1 | 10/2013 | Tousch et al. |
| 2014/0148880 | A1* | 5/2014 | Deisseroth ......... A61K 41/0038 607/100 |
| 2014/0273246 | A1* | 9/2014 | Bisso ................... G07D 7/0026 436/56 |
| 2015/0192518 | A1* | 7/2015 | Baxter .................... B01F 5/061 506/12 |

OTHER PUBLICATIONS

International Search Report and Written Opinion by International Searching Authority for International Application PCT/US2014/029487 dated Jul. 21, 2014 (10 pages).
International Search Report and Written Opinion by International Searching Authority for International Application PCT/US2014/029527 dated Oct. 9, 2014 (12 pages).
Appleyard, et al., "Bar-coded hydrogel microparticles for protein detection: synthesis, assay and scanning", Nature Protocols, Oct. 2, 2011, vol. 6, No. 11, pp. 1761-1774.
Battersby, et al., "Toward Larger Chemical Libraries: Encoding with Fluorescent Colloids in Combinatorial Chemistry", Journal American Chemical Society, Feb. 17, 2000, pp. 2138-2139.
Birtwell, et al., "Microparticle encoding technologies for high-throughput multiplexed suspension assays", The Royal Society of Chemistry, Integrative Biology, Jun. 2009, vol. 1, pp. 345-362.
Bogdan, et al., "Synthesis of Ligand-Free Colloidally Stable Water Dispersible Brightly Luminescent Lanthanide-Doped Upconverting Nanoparticles", Nano Letters (ACS), Jan. 18, 2011, vol. 11, pp. 835-840.
Bong, et al., "Hydrodynamic Focusing Lithography", Angewandte Chemie International Edition, Nov. 30, 2009, 49, pp. 87-90.
Bong, et al., "Non-polydimethylsiloxane devices for oxygen-free flow lithography", Nature Communications, May 1, 2012, 3:805, DOI: 10.1038/ncomms1800.
Braeckmans, et al., "Encoding microcarriers by spatial selective photobleaching," Nature Materials, Mar. 2003, vol. 2, pp. 169-173.
Cederquist, et al., "Encoded anisotropic particles for multiplexed bioanalysis", Wiley Interdisciplinary Reviews: Nanomedicin and Nanobiotechnology, Nov./Dec. 2010, vol. 2, pp. 578-600. First published online Jun. 8, 2010.
Chapin, et al., "Rapid microRNA Profiling on Encoded Gel Microparticles", Angewandte Chemie International Edition, Jan. 26, 2011, vol. 55, pp. 2289-2293.
Chapin, et al., "Ultrasensitive Multiplexed MicroRNA Quantification on Encoded Gel Microparticles Using Rolling Circle Amplification", Analytical Chemistry, Aug. 3, 2011, vol. 83, pp. 7179-7185.
Chen, et al., "Versatile Synthesis Strategy for Carboxylic Acid-functionalized Upconverting Nanophosphors as Biological Labels", Journal of the American Chemical Society, Feb. 16, 2008, vol. 130, pp. 3023-3029.
Choi, et al., "Multiplexed Detection of mRNA Using Porosity-Tuned Hydrogel Microparticles", Analytical Chemistry, Sep. 28, 2012, 84, pp. 9370-9378.
Cunin, et al., "Biomolecular screening with encoded porous-silicon photonic crystals", Nature Materials, vol. 1, pp. 39-41, Sep. 2002.
Dejneka, et al., "Rare earth-doped glass microbarcodes", Proceedings of the National Academy of Sciences, Jan. 21, 2003, vol. 100, No. 2, pp. 389-393.
Dendukuri, et al., "Continuous-flow lithography for high-throughput microparticle synthesis", Nature Materials, vol. 5, May 2006, pp. 365-369.
Dendukuri, et al., "Stop-flow lithography in a microfluidic device", Lab on a Chip, The Royal Society of Chemistry, May 21, 2007, vol. 7, pp. 818-828.
Fulton, et al., "Advanced multiplexed analysis with the FlowMetrix™ system", Clinical Chemistry 43:9; pp. 1749-1756, Sep. 1997.
Gerver, et al., "Programmable microfluidic synthesis of spectrally encoded microspheres", Lab on a Chip, The Royal Society of Chemistry, Sep. 25, 2012, 12, pp. 4716-4723.
Gorris et al., "Photon-upconverting nanoparticles for optical encoding and multiplexing of cells, biomolecules, and microspheres", Angewandte Chemie International Edition, 52 (13): pp. 3584-3600 (Feb. 28, 2013).
Gorris, et al., "Tuning the Dual Emission of Photon-Upconverting Nanoparticles for Ratiometric Multiplexed Encoding", Advanced Materials, Feb. 23, 2011, vol. 23, pp. 1652-1655.
Han, et al., "Quantum-dot-tagged microbeads for multiplexed optical coding of biomolecules", Nature Biotechnology, Jul. 2001, vol. 19, pp. 631-635.
Helgeson et al., "Hydrogel Microparticles From Lithographic Processes: Novel Materials for Fundamental and Applied Colloid Science", Current Opinion in Colloid & Interface Science, 16: 106-117 (Apr. 2011).
Kang, et al., "Digitally tunable physicochemical coding of material composition and topography in continuous microfibres", Nature Materials, Nov. 2011, vol. 10, pp. 877-883.
Kim et al., "Fabrication of low-cost submicron patterned polymeric replica mold with high elastic modulus over a large area", Soft Matter, 8, pp. 1184-1189 (Nov. 28, 2011).
Lee et al., "Colour-barcoded magnetic microparticles for multiplexed bioassays", Nature Materials, Letters, Sep. 2010, vol. 9, pp. 745-749.
Li Chunxia et al., "Upconversion nanoparticles for sensitive and in-depth detection of Cu2+ ions", Nanoscale, 4 (19), pp. 6065-6071 (Aug. 6, 2012).
Lin, et al., "Submicrometre geometrically encoded fluorescent barcodes self-assembled from DNA", Nature Chemistry, Oct. 2012, vol. 4, pp. 832-839.
Mahalingam, et al., "Colloidal Tm3+/Yb3+-Doped LiYF4 Nanocrystals: Multiple Luminescence Spanning the UV to NIR Regions via Low-Energy Excitation", Advanced Materials, Jun. 29, 2009, vol. 21, pp. 4025-4028.

(56) References Cited

OTHER PUBLICATIONS

Mandecki et al., "Light-Powered Microtransponders for High Multiplex-Level Analyses of Nucleic Acids", appears as Chapter 4 in Microfabricated Sensors by R. Kordal et al., ACS Symposium Series (Mar. 20, 2002), pp. 57-69.
Mitrelias et al., "Enabling suspension-based biochemical assays with digital magnetic microtags", Journal of Applied Physics, May 11, 2010, vol. 107, pp. 09B319-1 to 09B319-3.
Nicewarner-Pena, et al., "Submicrometer Metallic Barcodes", Science, vol. 294, Oct. 5, 2001, pp. 137-141.
Pregibon et al., "Multifunctional Encoded Particles for High-Throughput Biomolecule Analysis", Science, 315 (5817): pp. 1393-1396 (Mar. 9, 2007).
Vetrone et al., "The Active-Core/Active-Shell Approach: A Strategy to Enhance the Upconversion Luminescence in Lanthanide-Doped Nanoparticles", Adv. Func. Mater. 19: 2924-2929 (Jul. 16, 2009).
Wang et al, "Recent Advances in the Chemistry of Lanthanide-doped Upconversion Nanocrystals," Chemical Society Reviews, 38: 976-989 (Feb. 12, 2009).
Wang, et al., "Simultaneous phase and size control of upconversion nanocrystals through lanthanide doping", Nature, Letters, Feb. 25, 2010, vol. 463, pp. 1061-1065.
Wang, et al., Upconversion Multicolor Fine-Tuning: Visible to Near-Infrared Emission from Lanthanide-Doped NaYF4 Nanoparticles, Journal American Chemical Society, 2008, vol. 130, pp. 5642-5643.
Zhang et al., "Fluorescence upconversion microbarcodes for multiplexed biological detection: nucleic acid encoding", Advanced Materials, 23 (33), pp. 3775-3779 (Sep. 2011). (6 pages).
Zhang et al., "Rare-Earth Upconverting Nanobarcodes for Multiplexed Biological Detection", Small, 7(14): pp. 1972-1976 (Jul. 4, 2011).
Zhao, et al., "Microfluidic Generation of Multifunctional Quantum Dot Barcode Particles", Journal of the American Chemical Society, May 16, 2011, vol. 133, pp. 8790-8793.
Zhao, et al., "Multifunctional photonic crystal barcodes from microfluidics", NPG Asia Materials, Sep. 7, 2012, 4, e25; doi:10.1038/am212.46.
International Preliminary Report on Patentability by International Bureau of WIPO for International Patent Application No. PCT/US2014/029527 dated Sep. 15, 2015.
International Preliminary Report on Patentability by the International Bureau of WIPO for International Patent Application No. PCT/US2014/029487 dated Sep. 15, 2015.

\* cited by examiner

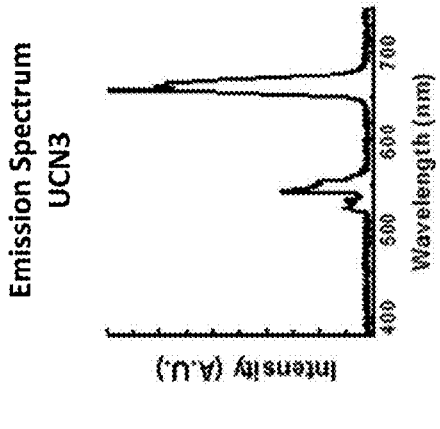
Fig. 2
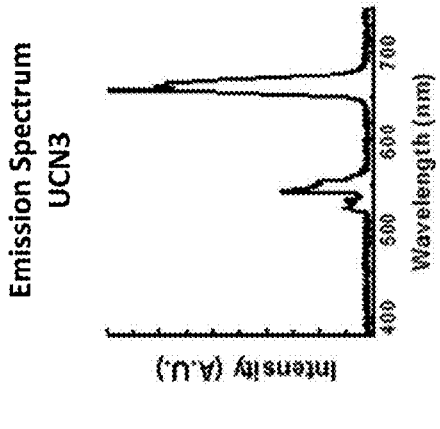
Fig. 3
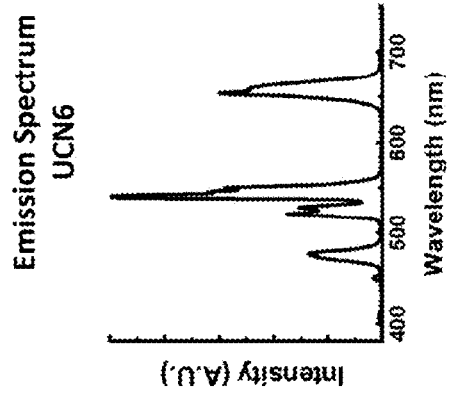
Fig. 4
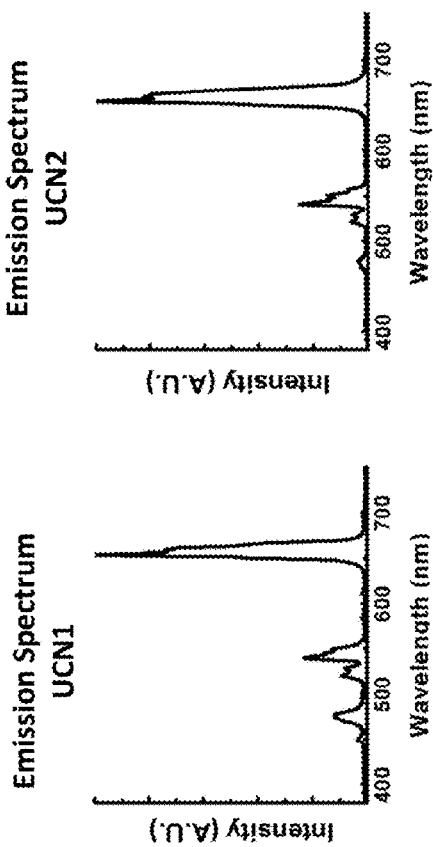
Fig. 5
Fig. 6
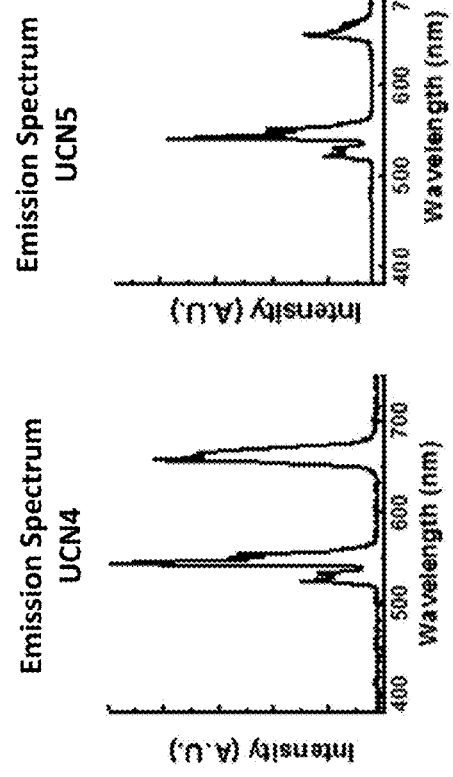
Fig. 7

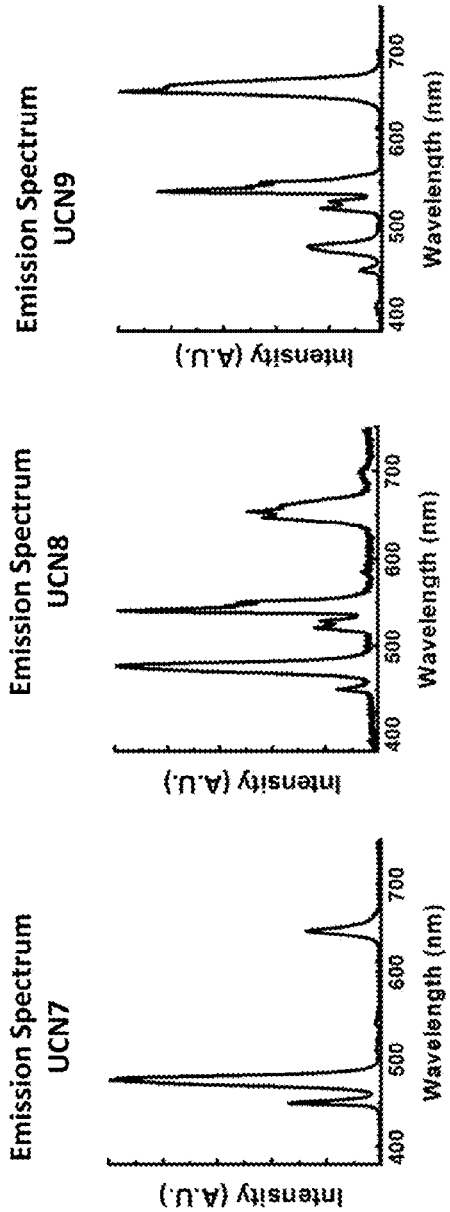
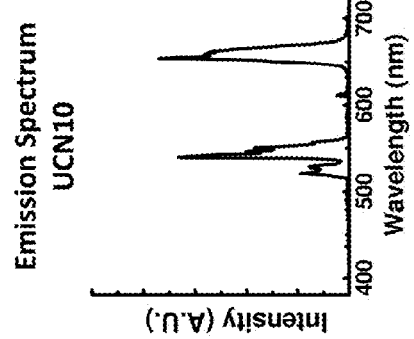
Fig. 8 Emission Spectrum UCN7
Fig. 9 Emission Spectrum UCN8
Fig. 10 Emission Spectrum UCN9
Fig. 11 Emission Spectrum UCN10

Second Code (47534)

ER1 – 4
ER2 – 7
ER3 – 5
ER4 – 3
PR – 221
ER5 – 4

First Code (45374)

| First Code (CDAEC) | 210 miRNA in sample | 221 miRNA in sample | Second Code (CEDAC) |
|---|---|---|---|
| | Yes | No | |
| | Yes | Yes | |
| | No | No | |
| | No | Yes | |

Fig. 35

RARE EARTH SPATIAL/SPECTRAL BARCODES FOR MULTIPLEXED BIOCHEMICAL TESTING

RELATED APPLICATIONS

The present application claims benefit of, and priority to U.S. Provisional Patent Application No. 61/801,351, filed Mar. 15, 2013, and U.S. Provisional Patent Application No. 61/800,995, filed Mar. 15, 2013, each of which is herein incorporated by reference in its entirety.

STATEMENT OF GOVERNMENT INTEREST

This invention was made with government support under Contract No. FA8721-05-C-0002 awarded by the United States U.S. Air Force and under Grant Nos. DMR-1006147 and CMMI-1120724 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Apr. 20, 2016, is named 122288-62002_SL.txt and is 1,297 bytes in size.

BACKGROUND

There are many different approaches currently being employed for performing multiplexed assays (e.g., two dimensional surface adsorbed arrays, fluorophore-bead systems, spatially-labeled microparticle systems). The multiplexing capabilities of these techniques may be insufficient to simultaneously probe some complex, heterogeneous biological systems.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 is a graph of an emission spectrum of exemplary upconversion nanocrystals (UCNs) labeled "UCN1", in accordance with an embodiment.

FIG. 3 is a graph of an emission spectrum of exemplary UCNs labeled "UCN2", in accordance with an embodiment.

FIG. 4 is a graph of an emission spectrum of exemplary UCNs labeled "UCN3", in accordance with an embodiment.

FIG. 5 is a graph of an emission spectrum of exemplary UCNs labeled "UCN4", in accordance with an embodiment.

FIG. 6 is a graph of an emission spectrum of exemplary UCNs labeled "UCN5", in accordance with an embodiment.

FIG. 7 is a graph of an emission spectrum of exemplary UCNs labeled "UCN6", in accordance with an embodiment.

FIG. 8 is a graph of an emission spectrum of exemplary UCNs labeled "UCN7", in accordance with an embodiment.

FIG. 9 is a graph of an emission spectrum of exemplary UCNs labeled "UCN8", in accordance with an embodiment.

FIG. 10 is a graph of an emission spectrum of exemplary UCNs labeled "UCN9", in accordance with an embodiment.

FIG. 11 is a graph of an emission spectrum of exemplary UCNs labeled "UCN10", in accordance with an embodiment.

FIG. 32 includes images of microparticles having two different codes under NIR illumination, in accordance with an embodiment.

FIG. 35 is a table with images of encoded microparticles used for multiplexed assays, in accordance with an embodiment.

Figure 1:
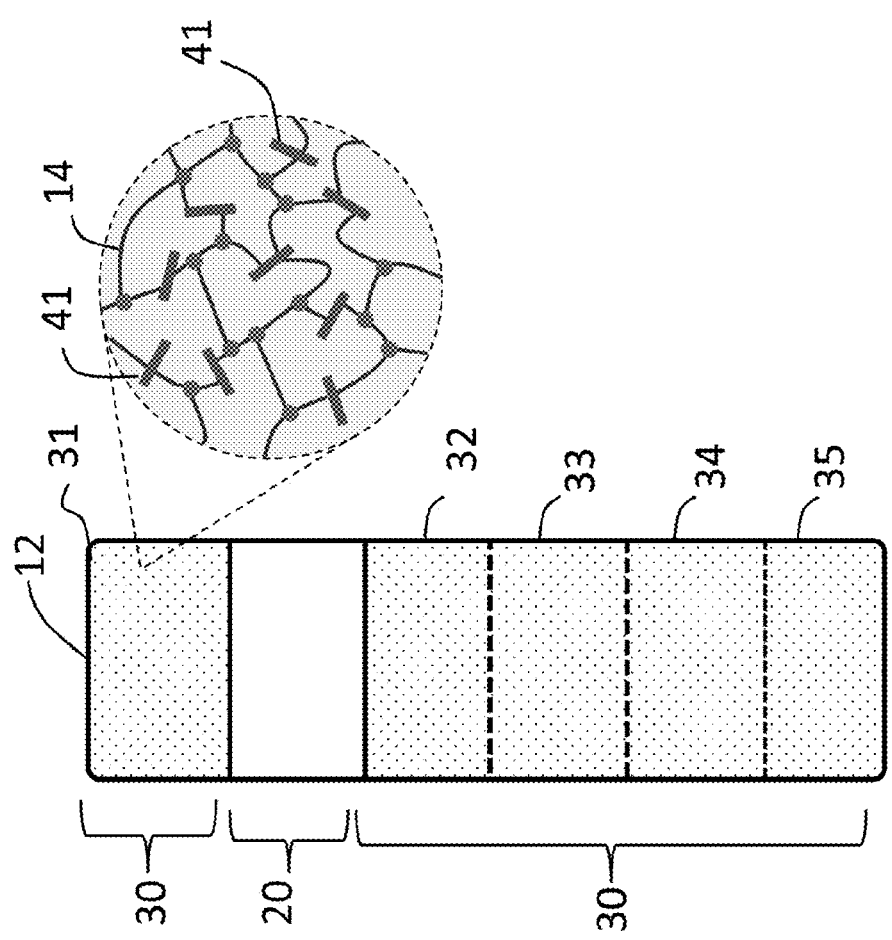
FIG. 1 schematically depicts an exemplary microparticle, in accordance with an embodiment.

Additional features, functions and benefits of the disclosed methods, systems and media will be apparent from the description which follows, particularly when read in conjunction with the appended figures.

DETAILED DESCRIPTION

Embodiments include hydrogel microparticles for use in biochemical or chemical assays, methods of producing the microparticles, and methods of performing biochemical or chemical assays using the microparticles. Each hydrogel microparticle has a probe region including one or more molecular recognition elements and an encoded region. The encoded region includes multiple portions, with each portion including an associated plurality of upconversion nanocrystals (UCNs) with a distinct spectral signature. The multiple portions of the encoding region enable spatial encoding of the microparticle. The associated plurality of UCN for each region are selected from a set of spectrally distinguishable UCN, which enables spectral encoding for each portion of the microparticle. By combining spatial and spectral encoding, the microparticles have massive multiplexing capabilities with superior scaling capability.

The coding scales exponentially as $C^S$ for asymmetric particles and as $C^S/2$ for symmetric particles, where C is the number of distinguishable spectral signatures (UCN 'colors') and S is the number of spatial features (e.g., microparticle 'stripes'). For example, for a symmetric microparticle with S encoding portions and a set of C different spectrally distinguishable UCNs, the following equation lists the number of codes or unique identifiers that would be available:

$$\sum_{x=0}^{S-1} C^{(S-x)}$$

For example, about 20,000 unique identifiers/codes can be generated for a system in which the encoding region of symmetric microparticles has six portions and each portion includes a plurality of UCN selected from a set of five different types of spectrally distinct UCNs. As another example, about 500,000 unique identifiers/codes can be generated for a system in which the encoding region of the symmetric microparticle has six portions and each portion includes a plurality of nanocrystals selected from a set of nine different types of spectrally distinct nanocrystals. Thus, a modest number of colors may be coupled with a similarly modest number of stripes to yield considerable encoding capacities that scale rapidly with incremental changes to either quantity. To increase the encoding capacity, asymmetric microparticles could be employed. For example, an asymmetric microparticle with six portions with each portion including one of nine different types of spectrally distinct nanocrystals would produce over a million unique identifiers/codes.

Some embodiments combine spatial patterning with rare-earth upconversion nanocrystals (UCNs), single wavelength near-infrared excitation and portable charge-coupled device (CCD)-based decoding to distinguish particles synthesized by means of flow lithography. Some embodiments exhibit large, exponentially scalable encoding capacities ($>10^6$), an ultralow decoding false-alarm rate ($<10^{-9}$), the ability to manipulate particles by applying magnetic fields, and dramatic insensitivity to both particle chemistry.

Some embodiments employ a robust encoding method for compatibility with high-throughput particle synthesis and portable CCD-based decoding. In some embodiments, the resulting particles and decoding system exhibit dramatic insensitivity to particle chemistry—enabling tuning of encoding capacity and decoding error rate independently of particle material properties—as well as the capacity for straightforward magnetic manipulation. In the examples described below, the inventors demonstrate quantitatively predictable decoding of both biocompatible particles in challenging, realistic environments. With single-particle encoding capacities in excess of 1 million and error rates of less than 1 part per billion (ppb), some embodiments expand the practically accessible number of codes for applications like multiplexed bioassays by orders of magnitude.

FIG. 1 schematically depicts an exemplary microparticle 10 for use in a biochemical or chemical assay, in accordance with an embodiment. The microparticle 10 has a body 12 including a hydrogel. The body 12 includes a probe region 20 and an encoded region 30. The probe region 20 includes one or more molecular recognition elements. The encoded region 30 includes multiple different portions (e.g., portions 31, 32, 33, 34, 34, 35) with each portion (31-35) having an associated plurality of upconversion nanocrystals (UCNs) (e.g., UCN 41) selected from a set of spectrally distinguishable UCN (see discussion accompanying FIGS. 2-11 below). In some embodiments, one or more portions may not include any nanocrystals and may serve as a "blank" or null portion for encoding. In some embodiments, the hydrogel body material is mesoporous to allow the diffusion of large (>10 nm) biomolecules though the hydrogel material).

For example, in some embodiments, a first plurality of UCNs with a first spectral signature is disposed in a first portion 31 of the encoded region. A second portion 32 of the encoded region includes a second plurality of UCNs with a second spectral signature different than the first spectral signature. In some embodiments, the encoded region of the microparticle also includes a third portion 33 having a third plurality of UCNs. In some embodiments, the encoded region of the microparticle also includes a fourth portion 34 having a fourth plurality of UCNs. In some embodiments, the encoded region of the microparticle also includes a fifth portion 35 having a fifth plurality of UCNs. The plurality of microparticles in each portion (31-35) of the encoded region is selected from a set of spectrally distinguishable UCNs.

One of ordinary skill in the art in view of the present disclosure would recognize that each microparticle may include an encoding region with fewer than five portions and associated pluralities of UCNs (e.g., four portions, three portions, two portions) or more than five portions and associated pluralities of UCNs (e.g., six portions, seven portions, eight portions, nine portions, ten portions, etc.).

The spectral signature associated with a plurality of UCN disposed in a portion of the encoded region is also referred to herein as the spectral signature of the portion of the encoded region. In some embodiments, two or more portions of the encoded region may have the same spectral signature. In some embodiments, two or more portions of the encoded region with the same spectral signature may be adjacent to each other. In some embodiments, any portions of the encoded region with the same spectral signature must be separated from each other by one or more portions of the encoded region having different spectral signature(s). In some embodiments, each portion of the encoded region must have a spectral signature different from that of every other portion of the encoded region. In some embodiments, one or more portions of the encoded region do not include UCNs so that the portion or portions is "blank" without a spectral signature.

The spectral signature of a UCN includes information associated with the emission spectrum of the UCN that distinguishes it from another type of UCN. In some embodiments, the spectral signature of a UCN or of a plurality UCNs of the same type may include the integrated intensity of emission of one spectral band (or emission in one spectral range) versus another spectral band (or emission in another spectral range). A spectral signature or information regarding a spectral signature may be referred to herein as a spectral code.

FIGS. 2-10 show emission spectra for an example set of nine spectrally distinguishable types of UCNs, labeled UCN1-UCN9 respectively, when excited with near infrared (NIR) light (e.g., 980 nm light from an NIR diode laser). UCNs in the example set luminesce in multiple narrow bands (e.g., bands less than 70 nm wide at full width half maximum (FWHM)) in the visible range when exposed to lower frequency (e.g., near infrared (NIR)) light. Specifically, the example set of spectrally distinguishable UCNs (e.g., UCN1-UCN10) emit in two or more bands centered around 470 nm (e.g., 445-500 nm), centered around 550 nm (e.g., 520-560 nm), and centered around 650 nm (e.g., 650-670 nm). For simplicity, the 445-500 nm band is referred to herein as the blue band, the 520-560 nm band is referred to herein as the green band, and the 640-670 nm band is referred to herein as the red band.

One of ordinary skill in the art in view of the present disclosure would recognize that the set of UCN may include fewer than nine (e.g., eight, seven, six, five, four, three, two) or more than nine (e.g., ten, nine, ten, eleven, twelve, etc.) different types of spectrally distinguishable UCNs. Further, one of skill in the art in view of the present disclosure would recognize that UCNs having different spectra than those shown, and UCNs than emit in different bands than those shown, also fall within the scope of embodiments. For example, FIG. 11 shows an emission spectrum for a UCN labeled UCN10 that may be used in the set as an alternative to any of UCN1-UCN9, or in addition to UCN1-UCN9. To augment encoding capacity, the palette of spectrally distinct UCNs may be further expanded by adjusting Yb—Er—Tm ratios with negligible impact on the decoding error rate.

The spectral signature of a plurality of UCNs may include information related to the ratio or ratios of the integrated intensities emitted in various bands (e.g., the ratio of the red band to the green band or vice versa, the ratio of the red band to the blue band or vice versa, the ratio of the blue band to the green band or vice versa, or any combination of the aforementioned). These ratios can be defined with respect to the emission spectra of the UCNs. However, in some embodiments, the spectral signature of a plurality of UCNs may include both information regarding the intensity of light emitted in various bands and include information regarding the responsivity of the image sensor to be used. Any detector, image sensor, or imaging device may be employed. For example, the detector or imaging device may be a charge-coupled device (CCD), a photomultiplier tube-based device (PMT), a complementary metal-oxide-semiconductor (CMOS) imaging sensor, an avalanche photodiode array (APD) imaging device, etc In some embodiments, an imaging sensor with more than one color channel may be employed.

Figure 13:
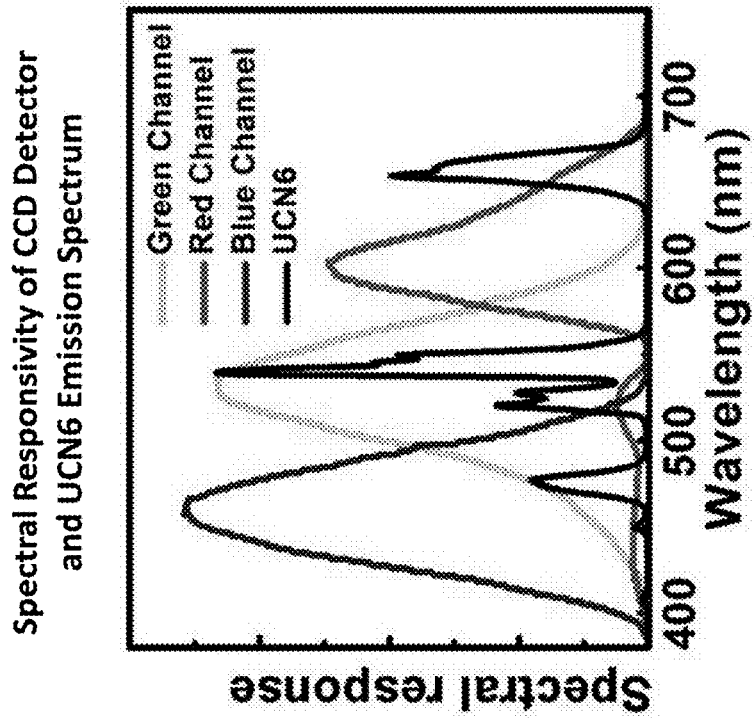
FIG. 13 is a graph of the emission spectrum of UCN6 overlaying the spectral responsivity of RGB channels of a CCD image sensor, in accordance with an embodiment.
Figure 12:
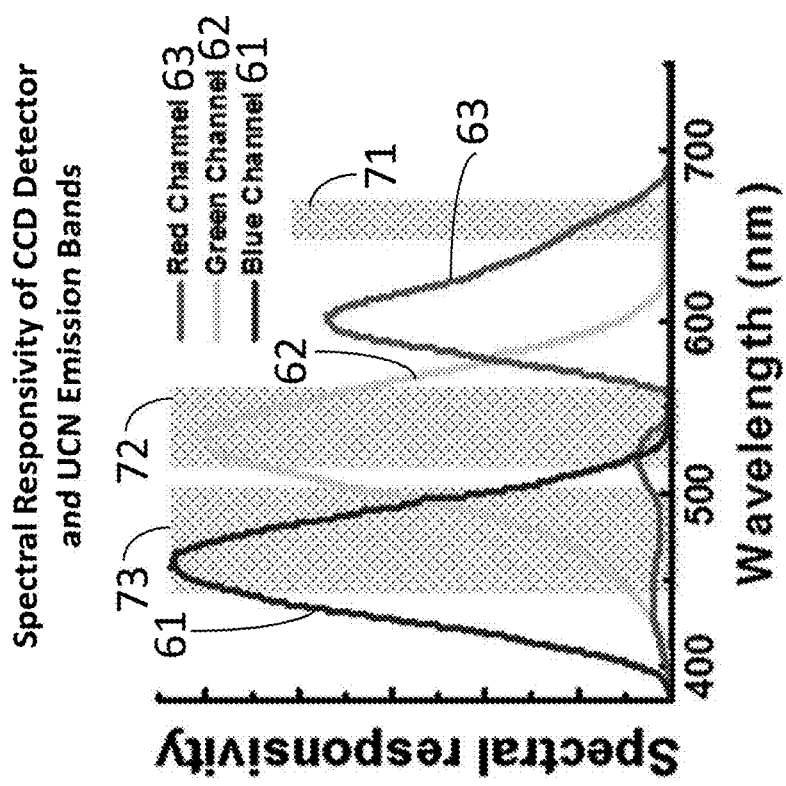
FIG. 12 is a graph of spectral responsivity of RGB channels of a CCD image sensor with UCN emission bands overlaid, in accordance with an embodiment.

FIG. 12 shows the spectral responsivity of red 61, green 62 and blue 63 channels for a typical RGB CCD device that may be used as a detector in some embodiments. As shown, the red 71, green 72, and blue 73 emission bands of the exemplary set of UCNs overlap the spectral responsivities of the respective red 61, green 62, and blue 63 channel responsivity curves. For example, FIG. 13 shows the emission spectrum of UCN6 overlaying the spectral responsivity of channels of a typical RGB device. A convolution of the emission spectrum with the expected spectral responsivity for each image sensor channel yields curves corresponding to the expected spectral response of each channel of the CCD image sensor to each type of UCN. The spectral signature for a type of UCNs can include information regarding the expected spectral response of an image sensor to a specific UCN emission spectrum, such as a ratio of the expected integrated intensity detected for two color channels.

For example, the Table 1 below shows the expected spectral response of a CCD device to the emission spectra of the UCN3-UCN7 and UCN10 types of UCNs (see FIGS. 4-8 and 11 for emission spectra). The expected spectral response is a convolution of the emission spectrum for type of UCN with the image sensor channel spectral responsivity shown in FIG. 12. Specifically, Table 1 shows the expected integrated total intensity for each color channel due to emission of the UCNs. Table 1 also includes ratios for the expected total intensity for the green channel to the red channel, for the blue channel to the red channel, and for the blue cannel to the green channel. Expressing the integrated intensities as ratios for different color channels reduces or eliminates the need for calibration to determine the absolute intensity for any particular color channel or emission band.

TABLE 1

| Type | Expected Integrated Intensity* R Channel | Expected Integrated Intensity G Channel | Expected Integrated Intensity B Channel | Channel Ratio G/R | Channel Ratio B/R | Channel Ratio B/G |
|---|---|---|---|---|---|---|
| UCN3 | 163.4 | 86.3 | 0 | 0.528 | 0 | 0 |
| UCN4 | 225.4 | 197.5 | 0 | 0.876 | 0 | 0 |

TABLE 1-continued

| Type | Expected Integrated Intensity* R Channel | Expected Integrated Intensity G Channel | Expected Integrated Intensity B Channel | Channel Ratio G/R | Channel Ratio B/R | Channel Ratio B/G |
|---|---|---|---|---|---|---|
| UCN5 | 91.9 | 164.5 | 0 | 1.790 | 0 | 0 |
| UCN7 | 24.7 | 52.1 | 219.9 | 2.109 | 8.9 | 4.220 |
| UCN6 | 138.5 | 158.1 | 120.4 | 1.141 | 0.869 | 0.7609 |
| UCN10 | 161.6 | 131.5 | 0 | 0.814 | 0 | 0 |

The inventors have found that employing UCN for identifying each encoded region of a particle has many benefits when compared with other techniques currently used for encoding particles. For example, some other techniques employ one-dimensional or two-dimensional thickness variations or holes in a fluorescently labeled coded region of a microparticle for identification.

In contrast with UCNs having multiple narrow emission bands, commonly used fluorescent labeling molecules (e.g., fluorophores) each tend to emit in a single broad band (e.g., DAPI fluorescent dye has a single emission band that is about 100 nm wide FWHM). In microparticles using fluorophores for encoding, the broad emission bands of the fluorophores limits the number of different fluorophores that may be employed without having significant overlap between emission bands and resulting ambiguity in identification. In addition, the absence of multiple emission bands for a single fluorophore may require the use of an external calibration standard. In contrast, UCNs have multiple narrow emission bands in different portions of the visible spectrum (e.g., separated by tens to hundreds of nm). The ratio of intensity of emission in various bands can be used to distinguish between different UCNs, and also acts as an internal calibration standard, obviating the need for external calibration.

Microparticles using UCNs for encoding may experience less reduction of the signal to noise ratio due to autoluminescence than microparticles using fluorophores for encoding. Luminescent UCNs absorb light in one range of wavelengths and emit light in a shorter range of wavelengths (e.g., absorb in the NIR range and emit in the visible range). In contrast, commonly used fluorophores and quantum dots usually absorb light in a wavelength range and emit light in a longer wavelength range (e.g., absorbing in the ultraviolet range and emitting in the visible range). For example, the commonly used fluorophore 4',6-diamidino-2-phenylindole (DAPI) has absorption maximum around 370 nm (UV) and an emission maximum around 450 nm (blue). Illumination of the fluorophores for identification (e.g., with UV light) may result in unintended autofluorescence of materials and solvents in the visible wavelengths that decreases the signal to noise ratio, which can be a significant problem with biological samples. Because the UCNs described herein are upconverting, the NIR light used to excite the UCNs generally does not cause autoluminescence in the shorter wavelengths of the visible range. Thus, the use of UCN may improve the signal to noise ratio for an encoded region.

Microparticles using different types of UCNs for encoding may require only a single narrow band excitation source as opposed to microparticles using different types of fluorophores, which may require multiple light sources to provide excitation in different wavelength bands. For example, a 980 nm light source with a power density of less than 10 W/cm$^2$ (e.g., an near infra-red (NIR) laser diode) may be used as a single excitation source for multiple different types of UCNs. In contrast, microparticles using common fluorophores for parts of the visual light spectrum, such as DAPI (blue), Oregon green 500 (green) and ALEXA FLUOR 633 (red) with absorption maximums at 350 nm, 503 nm and 632 nm, respectively, may require multiple different excitation sources such as a UV laser, an argon-ion laser, and a red helium-neon laser.

In some embodiments, the UCNs are rare-earth nanocrystals, which are bright anti-Stokes emitters with tunable spectral properties. Individual UCNs absorb continuous-wave (CW) NIR light at a single wavelength and emit in multiple narrow bands of the visible spectrum. Large anti-Stokes shifts reduce spectral interference from sample autofluorescence and lead to enhanced signal-to-noise ratios. In contrast to M-ink (an optically active dye in which nanostructured magnetic materials reflect different wavelengths of light) or quantum dots, these benefits persist even in the presence of obscurants or a complex reflective background. Tuning of emission intensities in multiple bands by adjusting relative stoichiometries of lanthanide dopants permits ratiometrically unique spectral encoding, in which the ratio of integrated intensities in two or more bands serve as the code, rather than absolute intensity. In some embodiments, external spectral standards (e.g., as required by porous silicon crystals), precise dye loading (e.g., as used with quantum dots and luminex), sensitive instrumentations (e.g. as required by M-Ink), and extensive calibration may be unnecessary for readout, enabling the use of standard CCD imaging for decoding.

Example Synthesis of UCNs

Lanthanide-doped NaYF$_4$ UCNs were made via a scalable batch hydrothermal synthesis, which is only one of numerous known protocols for synthesis of NaYF$_4$ UCNs. Aqueous rare-earth chloride salts, sodium hydroxide, ammonium fluoride, ethanol and oleic acid were heated in a TEFLON-coated stainless steel pressure vessel. Specifically, 2 ml of ReCl$_3$ (0.4 M, RE=Y, Yb, Er, Gd, Tm) and 2 ml of NH$_4$F (2 M) were added to a mixture of 3 ml of NaOH (0.6 M), 10 ml of ethanol and 10 ml of oleic acid. The solution was transferred to a 50 ml TEFLON-lined autoclave and heated at 200° C. for 2 hours. The resulting products were centrifuged to collect the UCNs, which were then repeatedly washed with ethanol and deionized water and then re-dispersed in cyclohexane.

During synthesis, the inventors used the concentration of various lanthanide dopants and the reaction time and temperature to improve the luminescence intensity of the UCNs and to alter the upconversion spectrum of the nanocrystals.

The synthesis procedure described above can produce NaYF$_4$ UCNs in two different phases having different crystal structures: an α-phase with a cubic crystal structure and a β-phase with a hexagonal crystal structure. Generally speaking, luminescence intensity is significantly higher in β-phase crystals than in α-phase crystals due to the lower ratio of surface defects to crystal volume in the β-phase. Without high levels of gadolinium doping, relatively high temperatures must be maintained for relatively long times (e.g., 350° C. for 24 hours) to induce the α→β phase transition in the UCNs. In contrast, the inventors doped with 30 mol % gadolinium (Gd) to induce the α→β phase transition at a lower temperature (200° C.) held for a shorter time (2 hours). The Gd has little to no effect on the shape of the upconversion emission spectrum generated due to the presence of the other dopants.

Increasing reaction time and increasing reaction temperature tended to increase the luminescence intensity of the UCNs due to increased nanocrystal size. Increasing the UCN size decreases the ratio of surface area to volume for the UCNs, thereby decreasing the ratio of surface defects to crystal volume. Further, luminescence for larger UCNs was less likely to be red-shifted due to preferential quenching of high frequency emission, which can occur in smaller UCNs.

Figure 14:
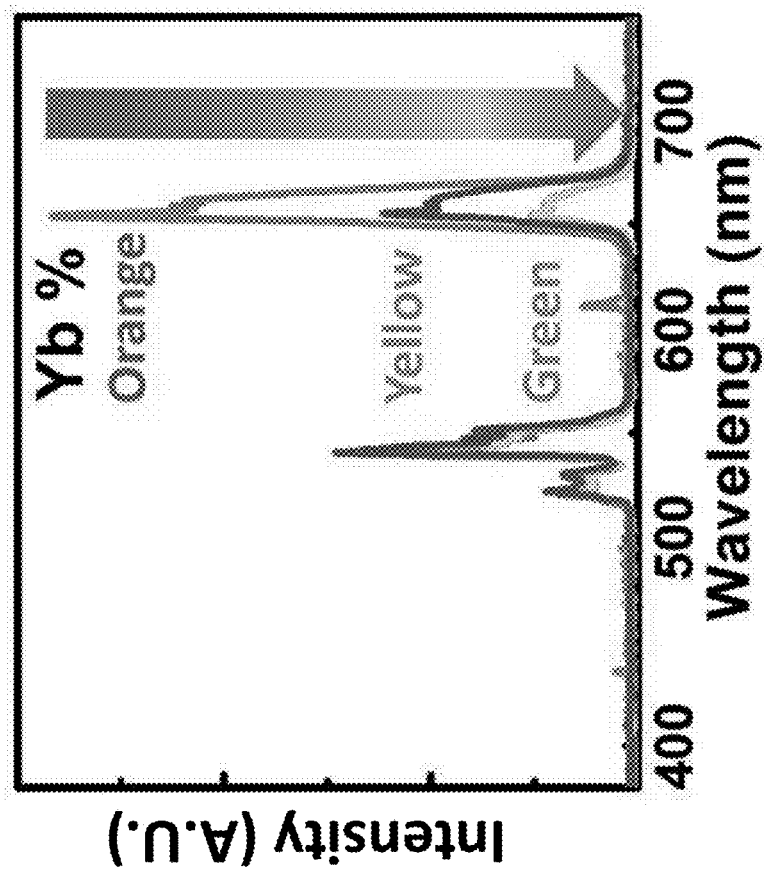
FIG. 14 is a graph showing unique upconversion emission spectra produced by varying dopant concentrations, in accordance with an embodiment.

The concentrations of dopants other than Gd were used to change the upconversion emission spectrum. Spectrally distinct UCNs were produced by adjusting the relative stoichiometries of the lanthanide ions $Yb^{3+}$, $Er^{3+}$ and $Tm^{3+}$ in the UCN reaction premix. The lanthanide dopant stoichiometries have relatively little impact on the UCN nanostructure and surface chemistry, decoupling control of the emission spectrum from the particle chemistry and resulting material properties. Ytterbium ($Yb^{3+}$) is an important dopant for bright multicolor emission, because it acts as a high-NIR absorption cross-section and energy transfer agent for upconverting emission. Increasing the Yb percentage tends to 'red-shift' the upconversion spectrum, increasing the ratio of the emission intensity in the red band (640-670 nm) relative to the emission intensity in the green band (520-560 nm) in Erbium ($Er^{3+}$) co-doped crystals. FIG. 14 illustrates how increasing the Yb concentration shifts the emission spectrum and shifts overall emission color from green to orange. Doping with $Er^{3+}$ at low levels (2% or less) leads to narrow peaks centered at 550 nm and 650 nm. Overall perceived emission color for materials doped with $Yb^{3+}$ and $Er^{3+}$ can range from green to red, depending on the Yb concentration. Doping with Thulium ($Tm^{3+}$) at very low levels (~0.2%) leads to emission in the blue band (445-500 nm) and a more intense peak at 800 nm.

Figure 15:
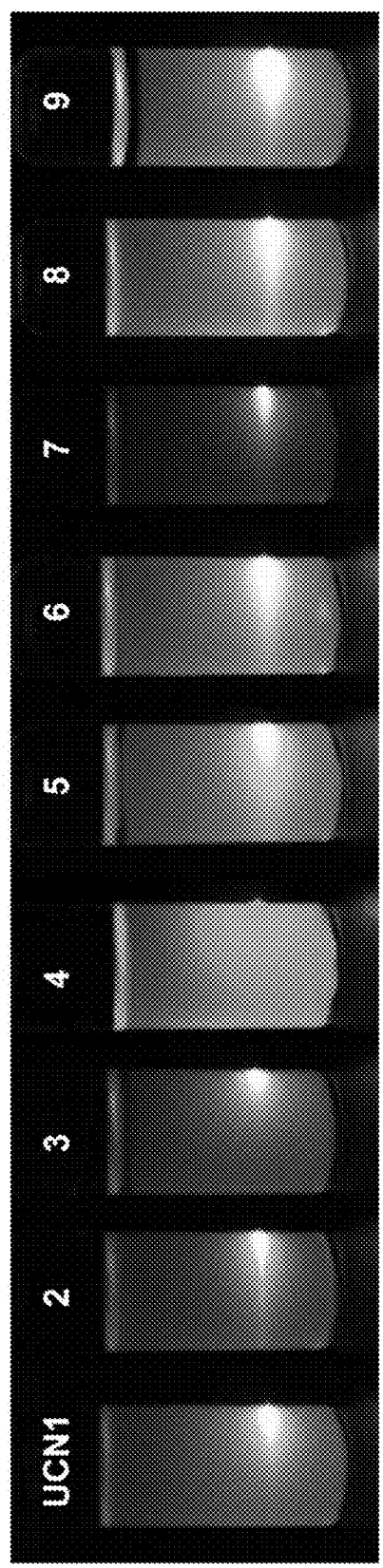
FIG. 15 is an image of different types of UCNs under NIR illumination, in accordance with an embodiment.

The inventors produced ten different types of spectrally distinguishable lanthanide-doped $NaYF_4$ UCNs labeled UCN1-UCN10, whose spectra appear in FIGS. 2-11. The overall colors of the UCN1-UCN9 types when irradiated with an NIR laser diode are shown in FIG. 15, which includes a luminescence image of suspensions of UCN1-UCN9 in cyclohexane upon 980 nm near infra-red (NIR) excitation. As illustrated by FIG. 15, the colors of the UCNs can be readily distinguished by the naked eye. The composition of the dopant used for each type of UCNs is listed in Table 2 below. The Y concentration, which makes up the balance of each dopant concentration, is in square brackets because it is not an active dopant.

TABLE 2

| Label | Gd (mol %) | Yb (mol %) | Er (mol %) | Tm (mol %) | [Y (mol %)] | Description of overall color |
|---|---|---|---|---|---|---|
| UCN1 | 30 | 69.7 | 0.1 | 0.2 | [0] | Violet |
| UCN2 | 30 | 69.9 | 0.1 | — | [0] | Red |
| UCN3 | 30 | 68 | 2 | — | [0] | Orange |
| UCN10 | 30 | 40 | 2 | — | [28] | Dark Yellow |
| UCN4 | 30 | 30 | 2 | — | [38] | Yellow |
| UCN5 | 30 | 18 | 2 | — | [50] | Green |
| UCN6 | 30 | 20 | 0.1 | 0.2 | [49.7] | Cobalt |
| UCN7 | 30 | 18 | — | 0.2 | [51.8] | Blue |
| UCN8 | 30 | 18 | 0.03 | 0.2 | [51.77] | Sky Blue |
| UCN9 | 30 | 31.7 | 0.1 | 0.2 | [38] | Grey |

Figure 16:
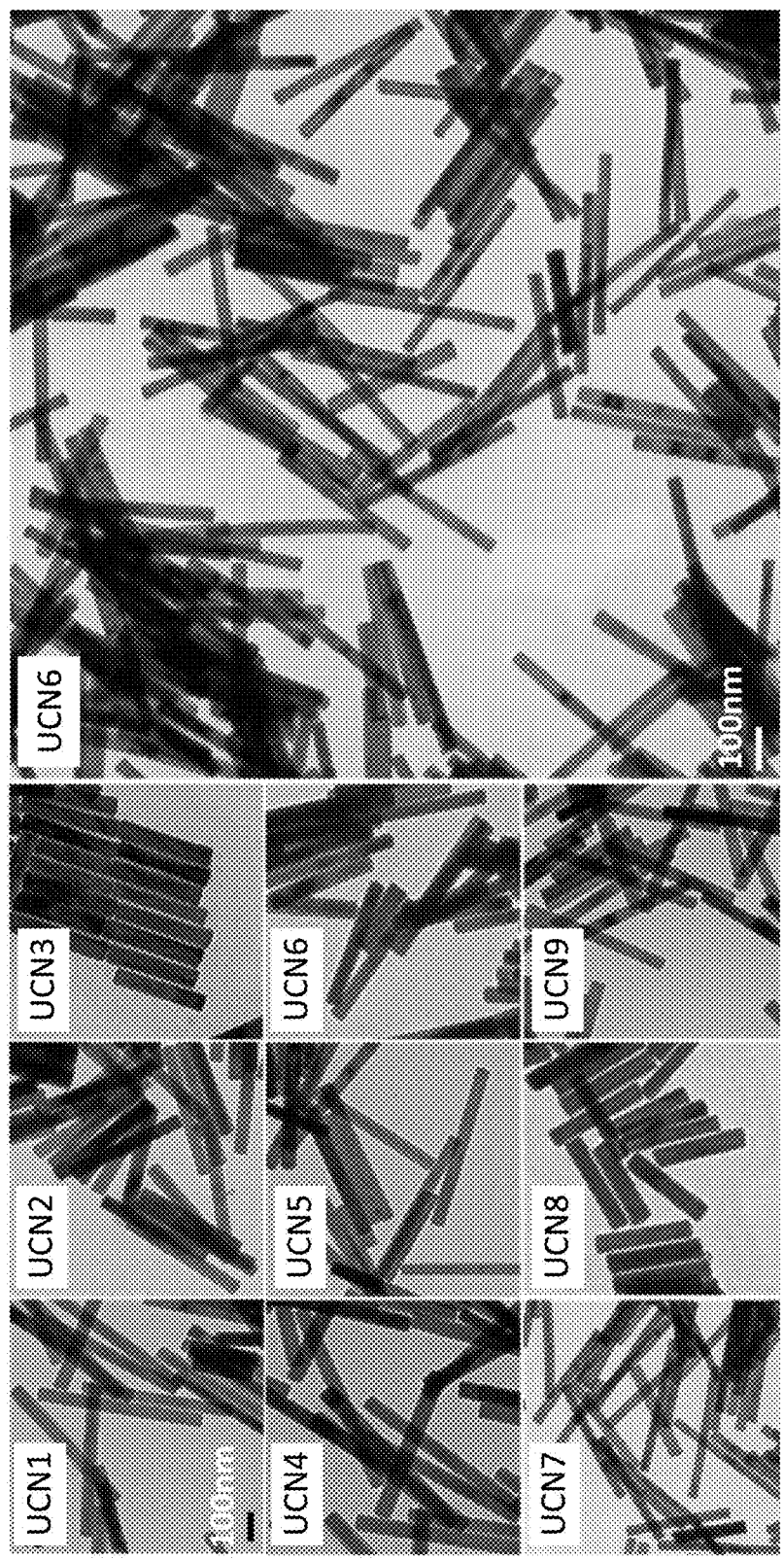
FIG. 16 is a transmission electron micrograph of different types of UCNs, in accordance with an embodiment.

FIG. 16 shows transmission electron microscopy (TEM) images of the UCN1-UCN9 types of UCNs produced by the process described above, as well as an enlarged image of the UCN6 nanocrystals. In FIG. 16, the scale bars are 100 nm. The TEM samples were prepared by placing a drop of UCNs in cyclohexane onto the surface of a copper grid. Overall, the UCNs produced were rod-shaped with an average size of 250-450 nm in length and 40-60 nm in width.

Figure 17:
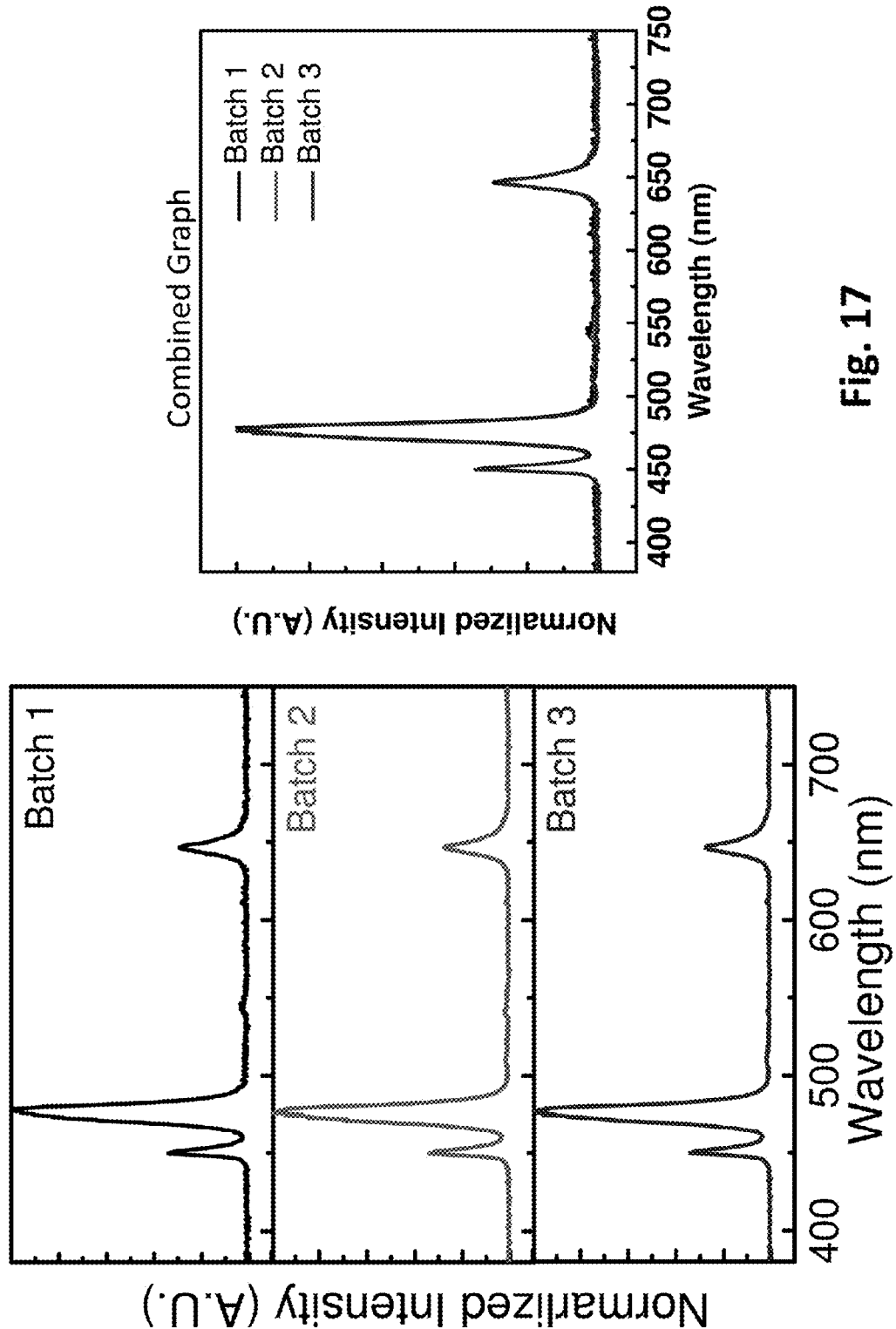
FIG. 17 includes graphs of emission spectra for different batches of UCNs, in accordance with an embodiment.

The inventors made several different batches of the same type of UCNs to confirm that the emission spectra were consistent from batch to batch. Upconversion luminescence spectra of UCNs were measured in a poly (urethane acrylate) (PUA) prepolymer solution (9/1 PUA/PI (v/v)) with a fluorescence spectrometer with a 1 W CW diode laser (980 nm) used as the excitation source. FIG. 17 shows the normalized emission spectra for three different batches of UCN7 type nanocrystal. As shown, emission spectra for the three different batches are practically indistinguishable on the combined graph.

Figure 18:
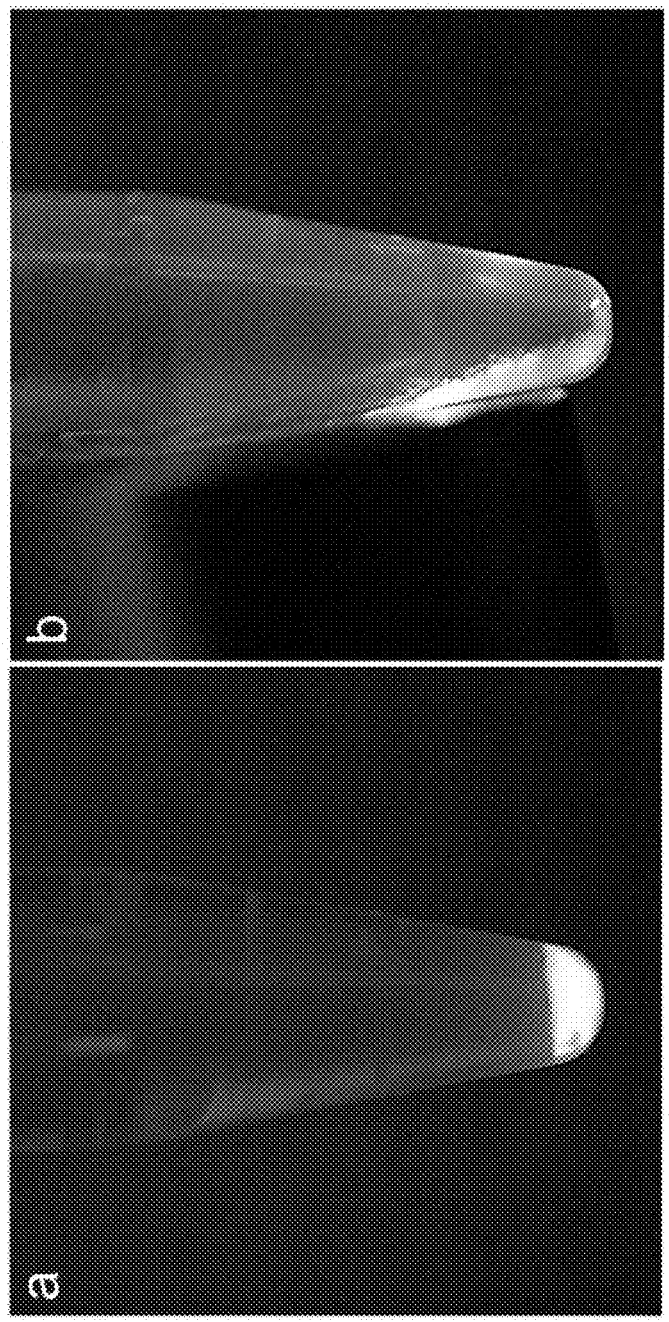
FIGS. 18a and 18b include luminescence images of UCNs in liquid with and without an applied external magnetic field, in accordance with an embodiment.
Figure 19:
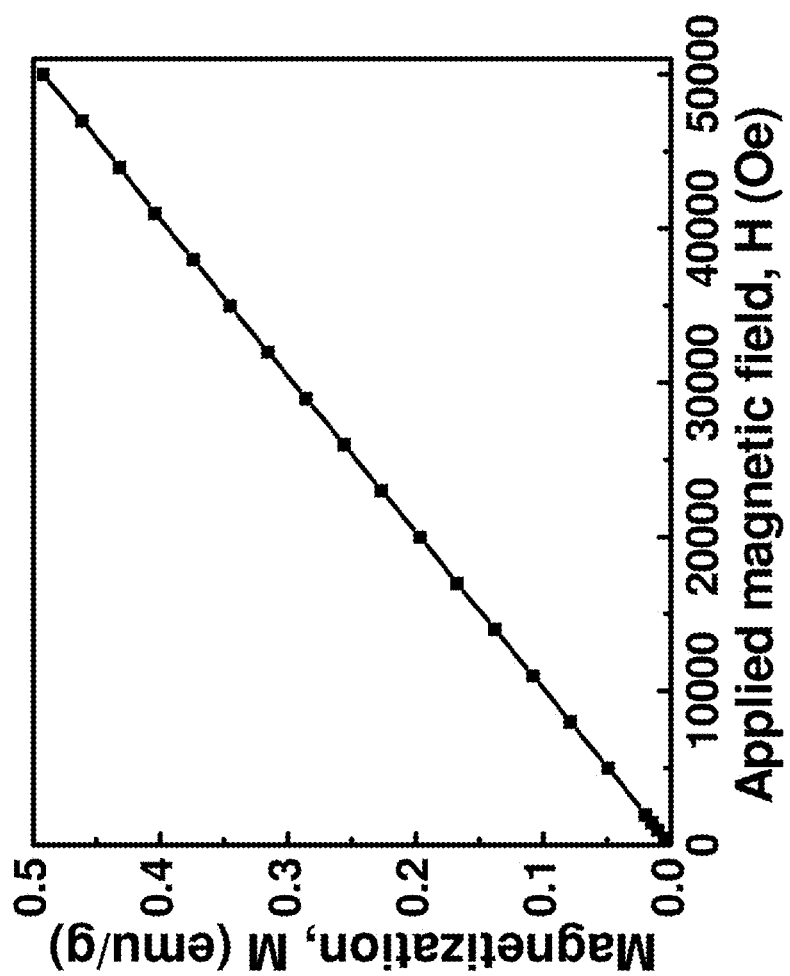
FIG. 19 is a graph of magnetization versus applied magnetic field for UCN4, in accordance with an embodiment.

The high Gd content of UCN1-UCN10 makes the UCNs paramagnetic and subject to physical manipulation through external magnetic fields. The inventors confirmed this by manipulating the nanocrystals suspended in vials using external ferromagnets. FIG. 18 includes luminescence images of UCNs in liquid in a vial (a) settled to the bottom of the vial with no applied magnetic field, and (b) with an applied magnetic field from a ferromagnet drawing the UCNs to the left side of the vial. FIG. 19 is a graph of data for magnetization as a function of applied magnetic field for UCN4, which was obtained using a superconducting quantum interference device (SQUID).

Example Surface Modifications of UCN

The synthesis process described above produced UCNs capped with oleic acid, a fatty acid with a 17-carbon hydrocarbon tail. As a result of the oleic acid capping, the resulting UCNs were insoluble in aqueous media, which created problems with dispersing the UCNs in aqueous or hydrophilic source materials. Furthermore, the UCNs with oleic acid tails luminesced brightly only in hydrophobic media. Exposure of the oleic acid capped UCNs to water caused significant aggregation and a high degree of reversible luminescence attenuation due to surface defect-mediated quenching.

The inventors utilized a method of modifying the oleic acid tail on the UCNs to improve their solubility in water and increase their luminescence in hydrophilic media. The oleic acid double bond was oxidized to form an alcohol, and then cleaved, thereby releasing the outward-facing hydrophobic part of the oleic acid chain and forming a carboxylic acid group.

The specific procedure employed to modify the oleic acid tail of the UCNs involved adding 0.1 gram of UCNs to a mixture of cyclohexane (100 mL), tert-butanol (70 mL), water (10 mL) and 5 wt % $K_2CO_3$ solution (5 mL) and stirring for about 20 minutes at room temperature. Then, 20 mL of Lemieux-von Rudloff reagent (5.7 mM $KMnO_4$ and 0.1 M $NaIO_4$ aqueous solution) was added dropwise to the solution. The resulting mixture was stirred for 48 hours. The product was centrifuged and washed with deionized water, acetone, and ethanol. Subsequently, the UCNs were dispersed in hydrochloric acid (50 mL) of pH 4, and stirred for 1 hour forming carboxyl-terminated UCNs, which were washed 5 times with deionized water and collected by centrifugation. The resulting carboxyl-terminated UCNs dispersed without aggregation in aqueous media and luminesced strongly in hydrophilic media.

The inventors developed a method for modifying the carboxyl-terminated UCN to form acrylate-terminated UCN that could be cross-linked with the hydrogel material of the microparticle. The method included mixing 200 μl of EDC (20 mg/ml) and 200 μl of sulfo-N-hydroxysuccinimide (sulfo-NHS) (20 mg/ml) with 200 μl of carboxy-terminated UCNs in 2-(N-morpholino) ethanesufonic acid (MES) buffer (0.1 M, pH 6.0, 40 mg/ml) and stirring for two hours at room temperature to activate the surface as carboxylic acid groups. The NHS-activated UCNs were centrifuged and washed with water. The precipitate was re-dispersed in 200 µl of PBS buffer (0.1 M, 5 ml, pH 7.2) containing 200 µl of 2-hydroxyethylacrylate (20 mg/ml). The mixture was then stirred for 24 hours at room temperature. The resulting acrylated UCN were purified by repeated centrifugation (3000 rpm, 5 min, 5 times) and resuspended in deionized water.

Figure 20:
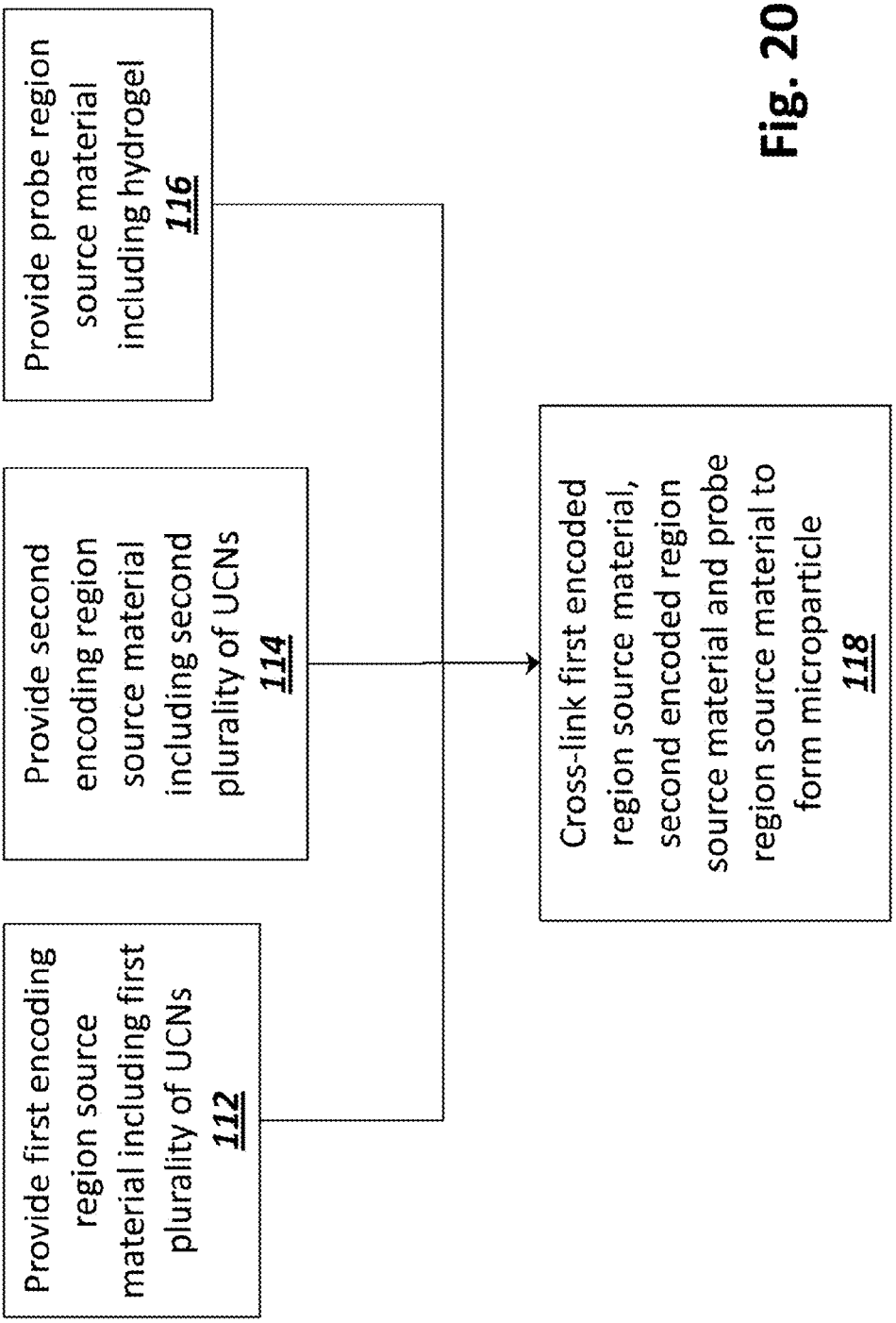
FIG. 20 is a block diagram schematically representing a method of forming a microparticle, in accordance with an embodiment.

FIG. 20 is a flow diagram 110 of a method of making a hydrogel microparticle for use in a biochemical or chemical assay. A first encoded region source material is provided (112). The first encoded region source material includes a hydrogel and a first plurality of UCNs having a first spectral signature. For example, the first plurality of UCNs may be the nanocrystals described above and labeled UCN3. The spectral signature of the first plurality of the UCNs (type UCN3) may be described as the spectrum shown in FIG. 4, or may be described by the ratio of the integrated intensity in one detection channel relative to another detection channel (e.g., the ratio of the green detection channel integrated intensity the red detection channel integrated intensity as shown in Table 1), or by multiple different integrated intensity ratios (e.g., green to red, blue to red, red to green). A second encoded region source material is also provided (114). The second encoded region source material includes a second plurality of UCNs having a second spectral signature different than the first spectral signature. The second plurality of UCNs may be the nanocrystals described above and labeled UCN4. The spectral signature of the second plurality of the UCN (type UCN4) may be described as the spectrum shown in FIG. 5, or may be described by the ratio of the integrated intensity in one detection channel relative to another detection channel (e.g., the ratio of the green detection channel integrated intensity the red detection channel integrated intensity as shown in Table 1), or by multiple different integrated intensity ratios (e.g., green to red, blue to red, red to green). Although the flow chart only specifies a first encoded region source material and a second encoded region source material, the number of encoded region source materials required corresponds to the number of portions of the encoded region desired in the resulting microparticle. A probe region source material including a hydrogel material is also provided (116).

The first encoded region source material, the second encoded region source material, and the probe region source material are cross-linked forming the first portion of an encoded region 31, the second portion of the encoded region 32, and the probe region 20. The probe region 20 is cross-linked with one or both of the first portion 31 and the second portion 32 of the encoding region to form a contiguous microparticle. In embodiments with more than two portions of the encoded region, each portion is cross-linked with one or more other portions of the encoded region and/or with the probe region.

In some embodiments, the UCNs for at least some of the portions of the encoded region have a hydrophilic surface. In some embodiments, the UCNs for at least some of the portions of the encoded region have a hydrophilic ligand. In some embodiments, providing the first encoded region source material and providing the second encoded region source material may include modifying the first plurality of nanocrystals and the second plurality of nanocrystals to have a hydrophilic surface and/or a hydrophilic ligand. Having a hydrophilic surface and/or a hydrophilic ligand may aid in dispersing the UCNs in the respective source material.

In some embodiments, the UCNs for at least some of the portions of the encoded region have acrylated ligands for cross-linking with the polymers of the hydrogel matrix. In some embodiments, providing the first encoded region source material and providing the second encoded region source material may include modifying the first plurality of nanocrystals and the second plurality of nanocrystals to include acrylated ligands. In some embodiments, the plurality of UCNs is bound to the polymer material at the time of particle synthesis through an acrylate group.

In other embodiments, another type of covalent linkage could be made between the UCNs and the hydrogel matrix. The UCNs can be bound to the hydrogel matrix using any number of covalent attachment mechanisms (e.g., amide linkages, disulfides, esters, ethers, aldehydes/ketones, cycloadditions, click chemistry, azides, and carbamates).

In some embodiments, at least some of the UCNs are doped with rare-earth metals. In some embodiments, at least some of the UCNs are doped with a composition including at least 30 mol % Gd. In some embodiments, at least some of the UCNs are paramagnetic.

In some embodiments, the material for each portion of the encoded region and for the probe region is the same material. In some embodiments, the material for the portions of the encoded region is different than the material for the probe region.

As noted above, in some embodiments, the UCNs have a hydrophilic surface. In some embodiments, the UCNs have a hydrophilic ligand. Having a hydrophilic surface and/or a hydrophilic ligand may aid in dispersing the UCNs in the source material.

In some embodiments, the method also includes co-flowing the source material for each encoded region and the source material for the probe region to an area for cross-linking. For example, a stop-flow lithography (SFL) technique may be employed for forming the microparticles. In SFL, viscous UV-sensitive pre-polymer solutions (which may be referred to herein as source materials) undergo laminar co-flow into a small microfluidic device, which may be made of polydimethylsiloxane (PDMS). For organic synthesis, the microfluidic device may be made from perfluoropolyether (PFPE). The flow of the pre-polymer solutions is stopped for a brief period in which the pre-polymer solutions in the device are exposed to photomask-patterned ultraviolet light. The UV light causes cross-linking, polymerization, or both within milliseconds in the region delineated by the photomask forming micro-sized polymeric particles. The shape of each particle is defined by the photomask. The composition of each striped portion of the particle is determined by the composition of the laminar co-flowing streams (e.g., the source materials). The SFL technique is particularly well suited for spatial and spectral encoding of microparticles using nanocrystals because of the ability to control both overall microparticle particle shape and the composition of different striped portions of the microparticle.

FIG. 15 schematically depicts SFL being used to make a hydrogel microparticle with a probe region and an encoding region with different portions of the encoding region including UCNs with distinguishable spectral signatures. In the diagram the encoded region source materials are labeled ERSM1-ERSM5, and the probe region source material is labeled PRSM. Each of the encoded region source materials includes a pre-polymer 142 and a plurality of UCNs, which may be acrylated UCN 144 in some embodiments. As used herein, the term pre-polymer includes monomers, and polymer chains that can be cross-linked. As used herein, the term cross-linking refers broadly to forming links between polymer chains, to forming links between a polymer and a nanoparticle, and to polymerization of monomers. The one or more encoded region source materials ERSM1-ERSM5 and one or more probe region source materials PRSM are flowed to an area 150 within a microfluidic device. When the co-flows are briefly stopped, a light source 160 (e.g., a 350 nm UV light source) a photomask 162 and a focusing optic (e.g., objective lens 164) provide patterned and focused light at the area 150 for cross-linking/polymerization of the pre-polymer 142. Cross-linking 146 of the pre-polymer source materials forms the microparticle 170 by creating a hydrogel polymer network. As shown, the UCNs 144 may include acrylated ligands, which allows the UCNs 144 to crosslink 146 with the hydrogel polymer network 148. Each encoded region source material ERSM1-ERSM5 forms a corresponding portion 171-175 of the encoded region and the probe region source material PRSM forms the probe region 180 of the microparticle 170. In some embodiments, the UCNs are not cross-linked with the hydrogel polymer network, but instead are physically entrained by the matrix pore size of the hydrogel polymer network.

Although photomask 162 is shown having a pattern that only forms one microparticle at a time, in some embodiments, the photomask may have a pattern for forming multiple microparticles simultaneously. In some embodiments, a photomask may have a pattern that produces microparticles having different shapes simultaneously. In some embodiments, the photomask may produce asymmetric particles and/or particles having nonrectangular shapes.

Figure 22:
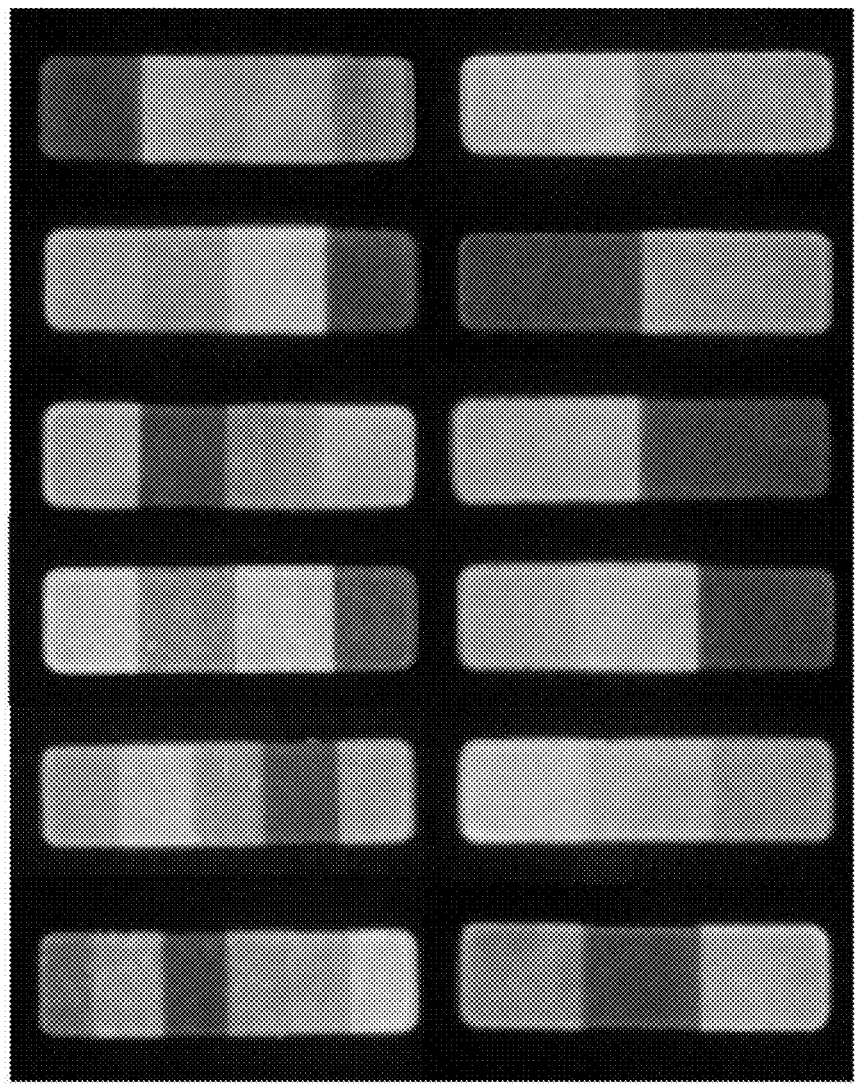
FIG. 22 is a luminescence image of microparticles having different numbers of encoded regions, in accordance with some embodiments.

Although microparticle 170 is shown with five encoded regions, in other embodiments, there may be more or fewer than six encoded regions. For example, FIG. 22 shows luminescence images of various microparticles each having between two to six encoded regions. Microparticles with an additional encoding region would boost the encoding capacity while requiring little more than an additional input port on the microfluidic synthesis device.

For further details regarding the SFL technique for forming hydrogel microparticles, see U.S. Patent Application Publication No. US 2012/0316082 A1, published Dec. 13, 2012, and U.S. Patent Application Publication No. US 2012/0003755 A1, published Jan. 5, 2012, each of which is incorporated by reference herein in its entirety. An exemplary flow lithography system is described below with respect to FIGS. 42 and 43.

Example Production of PEG-DA Hydrogel Microparticles with UCNs

Figure 23:
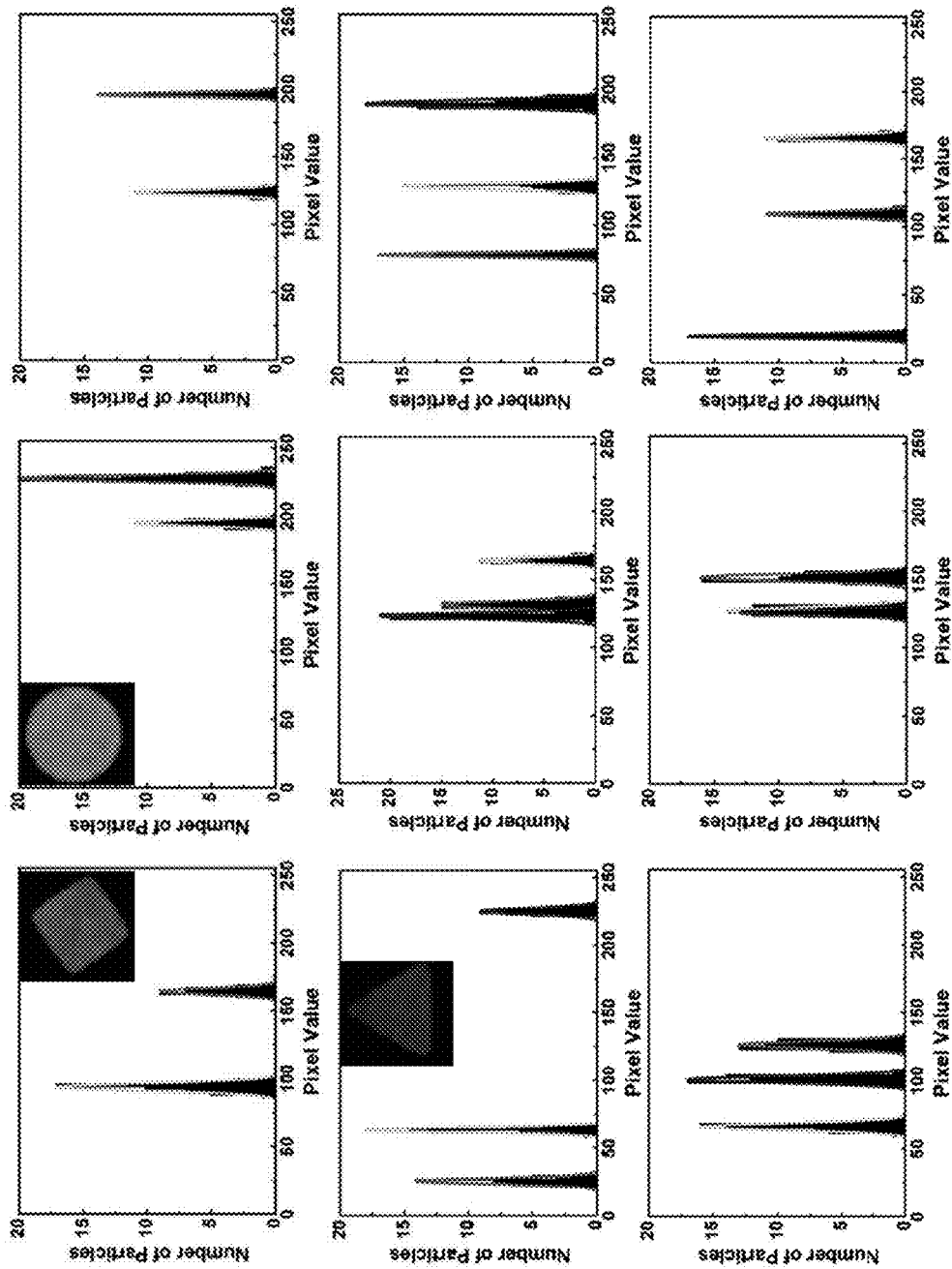
FIG. 23 includes graphs of integrated intensity values for microparticles, each including a different type of UCNs, in accordance with some embodiments.

The inventors produced polyethylene glycol diacrylate (PEG-DA) polymer microparticles by stop flow lithography. Initially, the inventors made sets of microparticles, with each set including only one type of nanocrystal to determine whether incorporating the nanocrystals into microparticles changes the emission spectral of the nanocrystals. For each of the nanocrystal types UCN1-UCN10, fifty PEG-DA hydrogel microparticles were produced. A CCD device was used to obtain a three color image (red channel, green channel and blue channel) of each microparticle while illuminated by NIR light producing a red channel image, a green channel image and a blue channel image. For each channel image, the intensity (pixel value) within the boundaries of each microparticle was integrated yielding a "pixel value" for each channel for each microparticle. FIG. 23 includes histograms of the integrated "pixel values" for the red, green and blue channels from fifty microparticles for the UCN1-UCN9 types. The histograms for some of the types also include an inset image of a representative NIR-illuminated microparticle. As shown by the inset images, a stop flow lithography process can be used to make different microparticle shapes.

The mean measured integrated intensity values from fifty microparticles for each type of UCNs were then compared with the expected integrated intensity data obtained from a convolution of the UCN emission data and the image sensor response curves. Table 3 below includes measured mean integrated intensity data, the standard deviation and the coefficient of variability for UCNs in microparticles. Expected integrated intensity data based on emission spectra from UCNs in solution are also included for comparison. As shown in the table, the mean integrated intensity and the expected integrated intensity values are consistent. The average coefficient of variation across all particles and UCN colors was 2%. This corresponds to an average standard deviation of 2.1 RGB units (on a scale of 255) for separately acquired images of separately synthesized particles, indicating outstanding particle-to-particle reproducibility. In addition, error ellipses are non-overlapping to better than 6 sigma, indicating that decoding error rates of less than 1 ppb are to be expected. Thus, if the emission spectrum of a type of nanocrystals is known, the integrated intensity for detection in a color channel can be reliably predicted.

TABLE 3

| Type | Expected Integrated Intensity | Mean Integrated Intensity ± standard deviation | Cv | Expected Integrated Intensity | Mean Integrated Intensity Channel | Cv | Expected Integrated Intensity ± standard deviation | Mean Integrated Intensity ± standard deviation | Cv |
|---|---|---|---|---|---|---|---|---|---|
|  | R | R | R | G | G | G | B | B |  |
| UCN1 | 130.3 | 126.34 ± 1.43 | 0.02 | 68.5 | 65.30 ± 2.29 | 0.03 | 103.7 | 100.74 ± 2.48 | 0.02 |
| UCN2 | 103.3 | 109.10 ± 1.87 | 0.01 | 44.8 | 42.70 ± 1.39 | 0.03 | 10.2 | 17.37 ± 1.43 | 0.08 |
| UCN3 | 164.5 | 164.29 ± 2.26 | 0.01 | 91.9 | 91.73 ± 2.73 | 0.02 | 0 | 0 | — |
| UCN10 | 161.6 | 160.86 ± 1.3 |  | 131.5 | 130.97 ± 1.3 |  | 0 | 0 | — |
| UCN4 | 225.4 | 225.89 ± 2.29 | 0.01 | 197.5 | 194.71 ± 2.01 | 0.01 | 0 | 0 | — |
| UCN5 | 91.9 | 86.10 ± 1.42 | 0.01 | 164.5 | 161.77 ± 1.89 | 0.01 | 0 | 0 | — |
| UCN6 | 120.4 | 123.52 ± 2.15 | 0.01 | 158.1 | 163.40 ± 2.04 | 0.01 | 138.5 | 132.29 ± 2.54 | 0.02 |
| UCN7 | 24.7 | 23.54 ± 2.02 | 0.08 | 55.1 | 63.22 ± 1.93 | 0.03 | 219.9 | 222.36 ± 2.9 | 0.01 |
| UCN8 | 83.2 | 78.37 ± 2.59 | 0.01 | 132.6 | 128.58 ± 2.63 | 0.02 | 182.2 | 189.61 ± 1.89 | 0.01 |
| UCN9 | 158.9 | 151.34 ± 2.02 | 0.01 | 131.1 | 127.62 ± 1.93 | 0.02 | 120.6 | 125.73 ± 2.92 | 0.02 |

Figure 24:
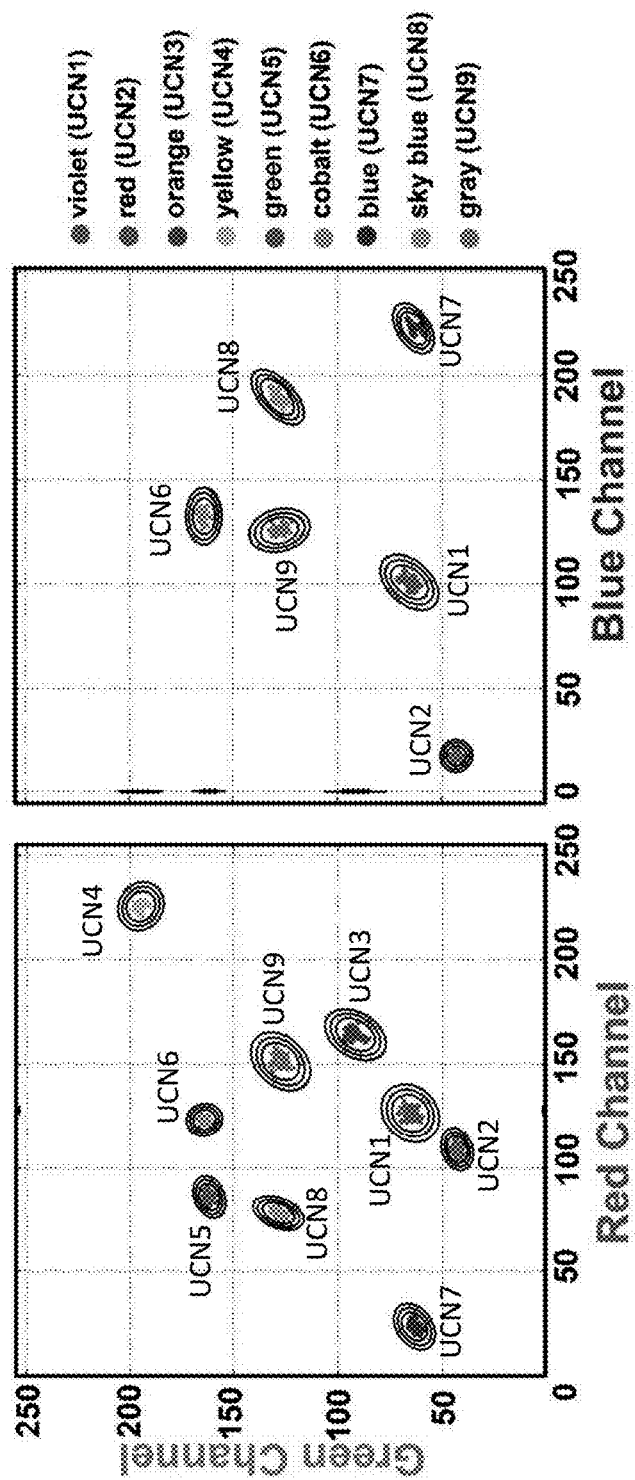
FIG. 24 is a scatter plot of integrated intensity data for microparticles including different types of nanocrystals, in accordance with some embodiments.
Figure 25:
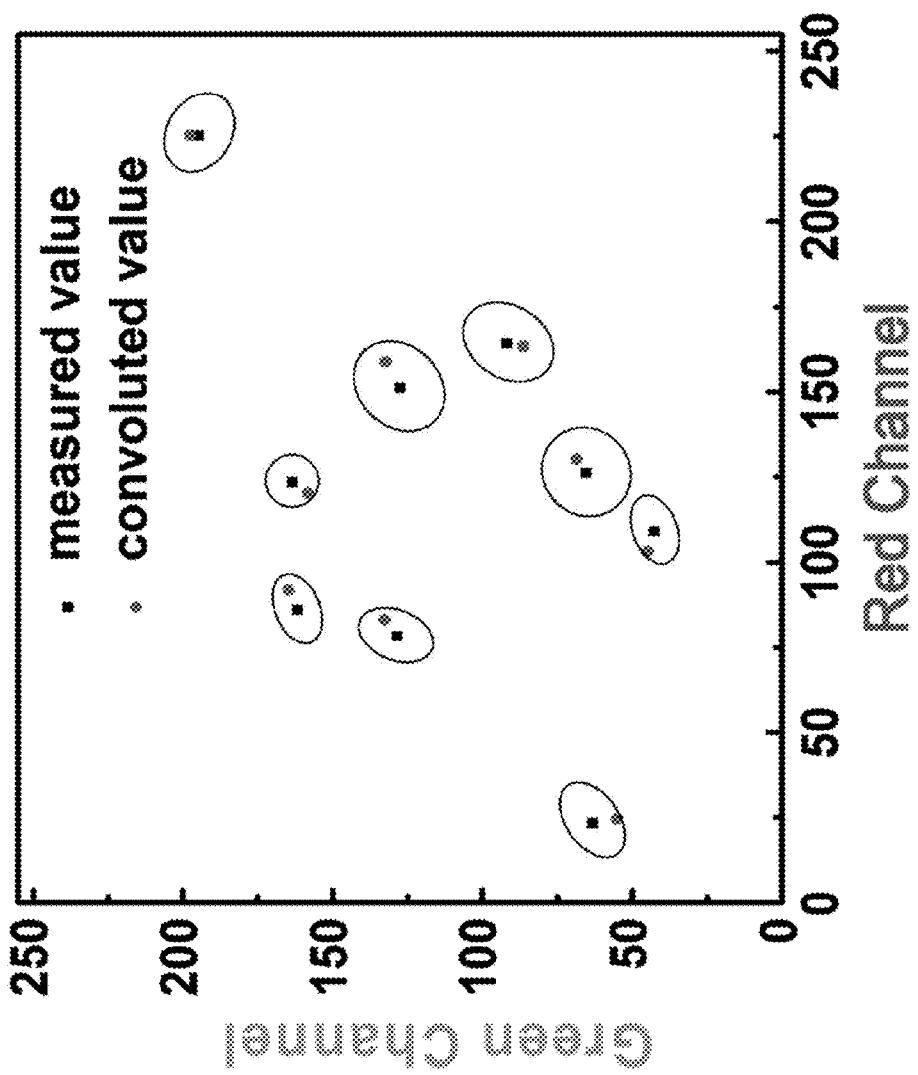
FIG. 25 is a plot of mean measured integrated intensity data and expected integrated intensity date for the red channel versus the green channel showing five-sigma confidence contours, in accordance with an embodiment.

FIG. 24 is a scatterplot showing the red channel, green channel, and blue channel integrated intensity values for each microparticles incorporating the UCN1-UCN9 type nanocrystals. All of the UCN1-UCN9 types of nanocrystals have red channel and green channel emission intensities. The UCN1, UCN2, UCN6, UCN7, UCN8 and UCN9 types of nanocrystals have emission intensities in the blue channel as well as the red and green channels. The ellipses around each cluster of data points are the three-sigma, four-sigma and five-sigma contours derived from fitting a Gaussian mixture model to the data. As shown by separation between the tight clusters, the UCN type for each microparticle can clearly be distinguished using the red channel, green channel, and blue channel integrated intensities for the microparticle. FIG. 25 shows a comparison of the mean integrated intensity value (measured value squares) and the expected integrated intensity value (convoluted value circles) in the green channel versus the red channel for particles integrating UCN1-UCN9 types of nanocrystals. The ellipses represent the five-sigma confidence contours.

Thus, the inventors demonstrated noise-robust spectral discrimination of six different types of UCNs in hydrogel particles illuminated using an NIR diode laser and imaged using a standard CCD camera. Further, as shown by the green channel vs. red channel plot, the red channel integrated intensity and the green channel integrated intensity are sufficient to distinguish between the six different types of nanocrystals. The FIGS. 24 and 25 scatter plots reveal that cluster overlap occurs only past six standard deviations from the mean, implying an expected error rate of less than 1 part per billion (ppb).

Figure 26:
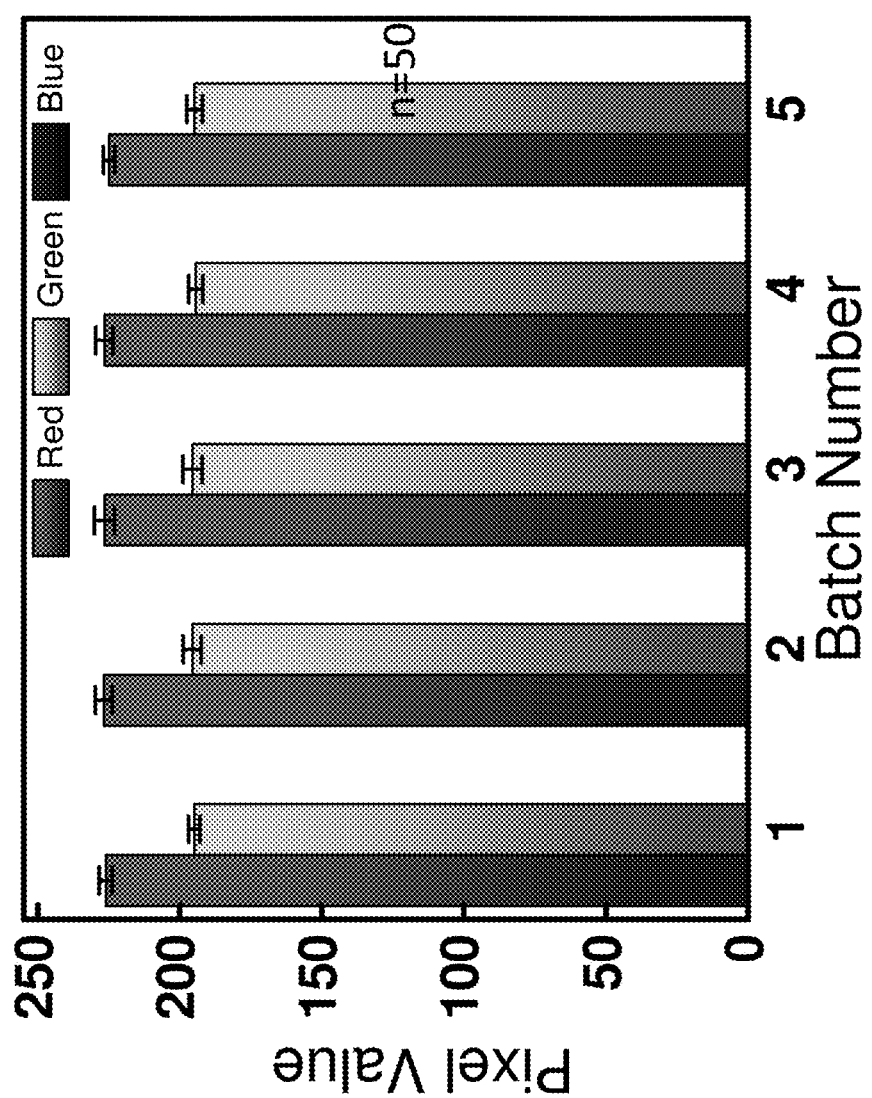
FIG. 26 shows integrated intensity data for different batches of microparticles, in accordance with some embodiments.

The inventors also compared different batches of hydrogel microparticles produced at different times to determine the reliability and the predictability of the integrated intensities of microparticles from different batches. Five separate batches of fifty microparticles were produced, each batch including the same UCN4 type nanocrystals. The microparticles were illuminated with an NIR light source and color images were obtained using a CCD camera. Integrated intensity data was generated for microparticles in all five batches and the average integrated intensity values for each batch were compared. FIG. 26 is a graph comparing the average integrated intensities for the green channel and for the red channel for each batch of fifty microparticles. The integrated intensities in the red and green channels were consistent across the five batches. As expected, there was no detected signal the blue channel. Table 4 below lists the measured red and green channel integrated intensity values for each batch showing the consistency and reproducibility of the spectral signature for different batches of microparticles.

TABLE 4

| Type | Red Channel Mean Integrated Intensity ± standard deviation | Green Channel Mean Integrated Intensity ± standard deviation |
|---|---|---|
| 1 | 225.89 ± 2.29 | 194.71 ± 2.01 |
| 2 | 226.51 ± 2.97 | 195.46 ± 3.14 |
| 3 | 226.35 ± 3.42 | 195.36 ± 3.34 |
| 4 | 226.36 ± 3.01 | 194.22 ± 2.46 |
| 5 | 224.65 ± 2.05 | 194.68 ± 2.77 |

Figure 27:
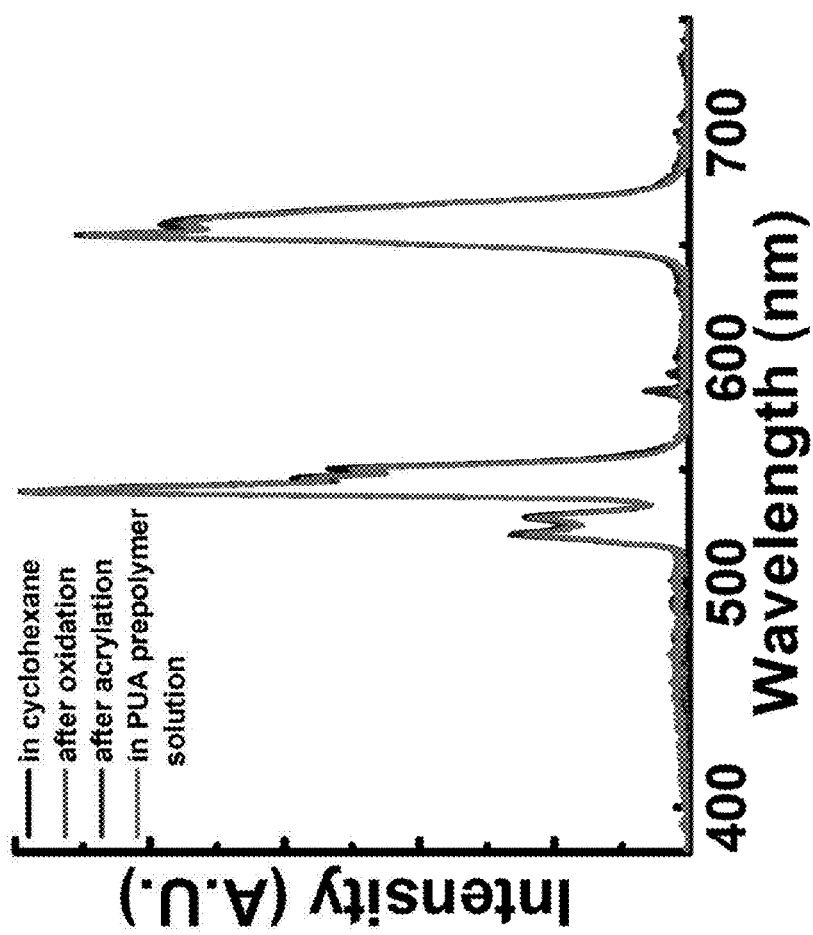
FIG. 27 is a graph of emission spectra of UCN4 after each step in surface chemical modification of the UCNs, in accordance with some embodiments.

The inventors confirmed that the oxidation and acrylation process does not change an emission spectrum of the UCNs. FIG. 27 is a graph of emission spectra of UCN4 type nanocrystals after each step in the surface chemical modification of the UCNs (e.g., before processing in cyclohexane, after oxidation, after acrylation, and in PUA prepolymer solution). The spectra overlay each other establishing that surface chemistry modifications of the UCNs before incorporation into microparticles does not significantly affect emission spectra of the resulting particles.

Figure 28:
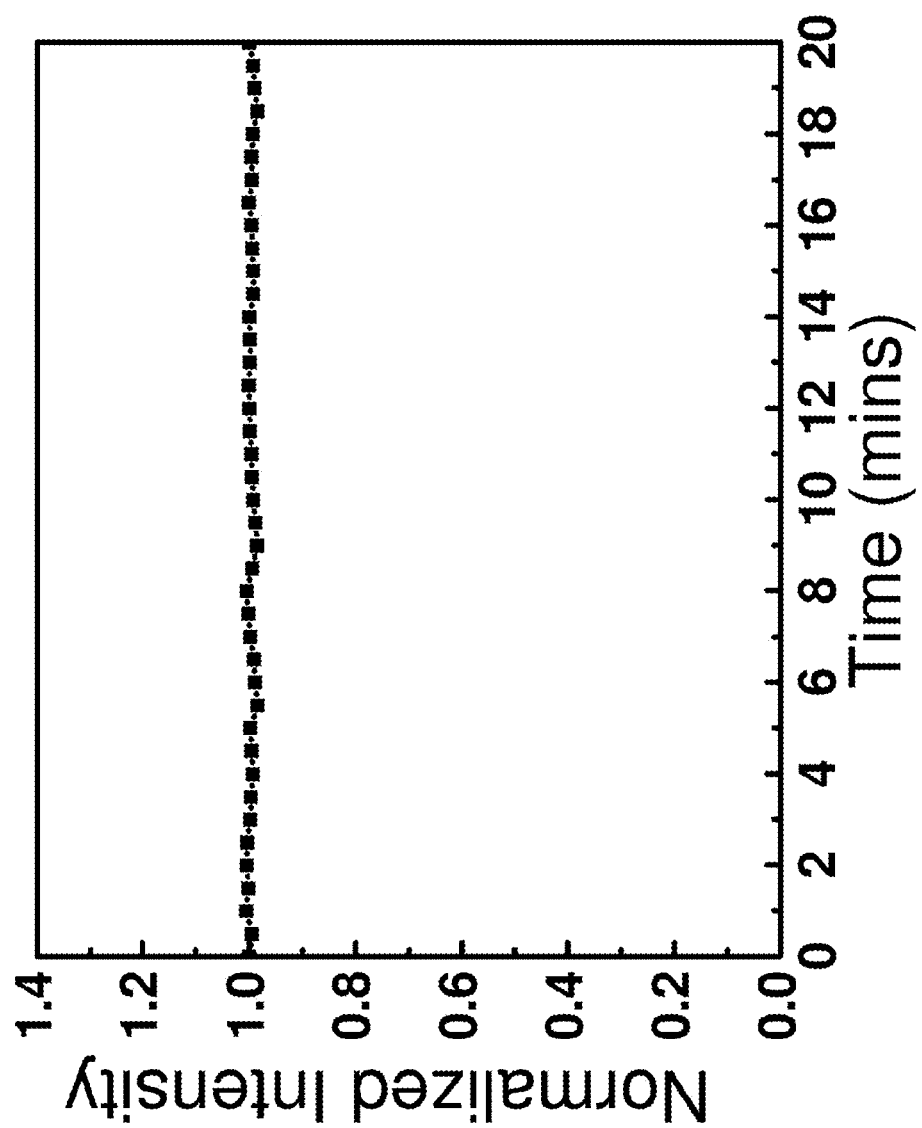
FIG. 28 shows microparticle emission intensity as a function of time during intense sustained NIR irradiation, in accordance with some embodiments.

The inventors also confirmed that there was no attenuation of the luminescence response of the UCNs integrated into hydrogel microparticles upon prolonged intense NIR irradiation due to photobleaching. FIG. 28 is a graph of intensity as a function of time for hydrogel microparticles including UCN7 type nanocrystals upon continuous exposure to a 980 nm NIR light from a 1 W laser. This is in contrast to many commonly used fluorophores which exhibit attenuation due to photobleaching.

Figure 29:
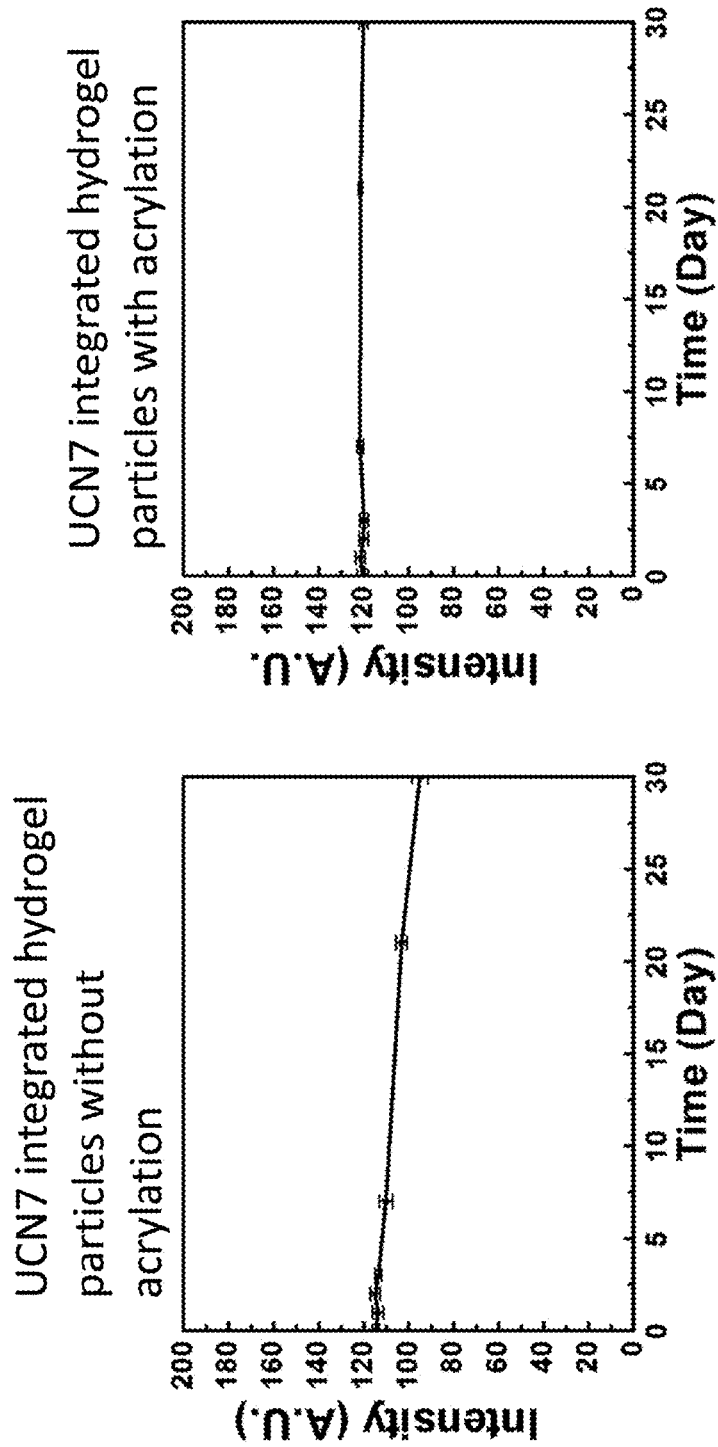
FIG. 29 shows graphs of intensity versus microparticle age for microparticles with carboxyl-terminated UCN and for microparticles with acrylated UCN, in accordance with some embodiments.

The inventors also compared the stability of hydrogel microparticles made with carboxyl-terminated UCNs, in which the nanocrystals are trapped in pores in the hydrogel matrix, and hydrogel particles made with acrylated UCNs, in which the nanocrystals are bonded to the hydrogel matrix via acrylates. FIG. 29 includes graphs comparing intensity as a function of age of microparticles including acrylated UCN7 type nanocrystals and microparticles including carboxyl-terminated UCN7 type nanocrystals without acrylation. As shown, there is a reduction in emission intensity of the microparticles including carboxyl-terminated UCNs without acrylation over 30 days, presumably due to the UCNs diffusing out of the microparticles. In contrast, the microparticles with acrylated UCNs showed no attenuation over 30 days of aging. Thus, acrylation of the UCNs and subsequent bonding to the hydrogel matrix improves the luminescence stability (e.g., the shelf-life) of the microparticles.

Example Formation of PEG-DA Hydrogel Microparticles with Spectral and Spatial Encoding After establishing the predictability and reproducibility of the method for forming UCNs and the predictability and reproducibility of the spectra from hydrogel particles that each include only one type of UCNs, the inventors produced PEG-DA hydrogel microparticles with both spectral and spatial encoding. PEG-DA microparticles are biocompatible and mesoporous allowing diffusion of large biological macromolecules. Stable integration of UCNs into microparticles involved use of hydrophilic surface chemistry with a UV-active functional group on the UCNs for strong, covalent incorporation as described above. In an embodiment in which the hydrogel is more densely cross-linked covalent incorporation of the UCNs may not be needed. In an embodiment in which the UCNs are disposed in a non-hydrogel portion of the particle, covalent incorporation of the UCNs may not be needed. For example, in microparticles with a hydrogel probe region and a PUA encoded region, the dense cross-linking of the PUA and the hydrophobic surface chemistry large, rod-like UCN nanostructure may enabled homogeneous and irreversible physical entrainment of the UCNs in the PUA portion.

Specifically, elongated hydrogel microparticles were produced that each included a probe region and an encoding region. The encoding region was divided into five portions, (e.g., five stripes) with each portion including a plurality of UCNs having distinguishable spectral signature. Although the microparticles produced included five portions of a encoded region, in some embodiments, each microparticle may have an encoded region with more than five portions or less than five portions. Although the hydrogel microparticles produced were rectangular and elongated, in some embodiments, the hydrogel microparticles may have a different aspect ratio and/or a different shape. Further, the microparticles produced may be symmetric or asymmetric.

The microparticles were produced by SFL using encoding region source materials and a probe region source material. Specifically, for each encoding region source material, acrylated UCN were dispersed in a PEG-DA premixture solution yielding a mixture of 45 vol % PEG-DA (Mn=700), 40 vol % UCNs (0.5 mg/µl) 10 vol % poly(styrenesulfonate) PSS and 5 vol % DAROCUR 1173 photoinitiator (PI)). For microparticles with a PUA encoded portion, the PUA microparticle source material comprised 150 mg of UCNs dispersed in 300 µl of a 9:1 volume ratio PUA/PI solution.

Figure 21:
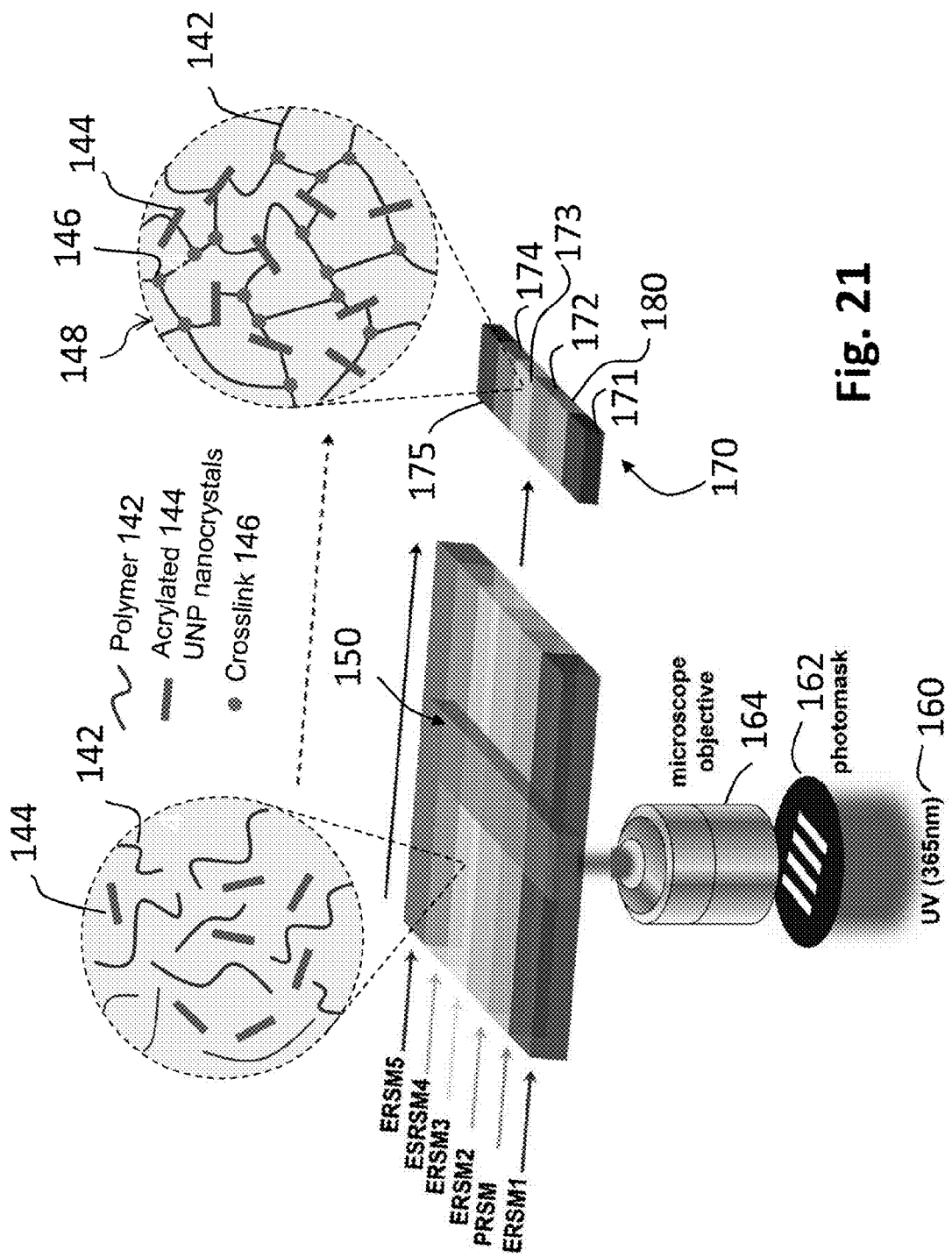
FIG. 21 schematically depicts a stop flow lithographic method of forming a contiguous microparticle, in accordance with an embodiment.

The probe region source material employed a similar PEG-DA premixture solution that also included molecular recognition element, specifically a nucleic acid probe for miRNA target molecules. The source materials were used to form microparticles using SFL as described above with respect to FIG. 21.

A microfluidic device was fabricated from poly-dimethylsiloxane (PDMS) for the SFL system. PDMS was mixed with a curing agent in a 10:1 ratio and degassed under vacuum for 30 min. Degassed PDMS was poured onto an SU-8 master mold and cured overnight at 65° C. Channels were then cut out of the mold and bonded with a glass slide coated with partially-cured PDMS in order to assure oxygen permeability. The assembled device was fully cured overnight at 65° C. The microfluidic channel in the microfluidic device of the SFL system was 300 µm wide and 36 µm high.

A photomask for the SFL was designed using a computer added drafting program and printed with a high-resolution printer. The mask was placed in the field-stop of a microscope before synthesis. A microfluidic device was fabricated from poly-dimethylsiloxane (PDMS) for the SFL system. PDMS was mixed with a curing agent in a 10:1 ratio and degassed under vacuum for 30 min. Degassed PDMS was poured onto an SU-8 master mold.

The microfluidic channel of the SFL system was loaded with the composite monomer solution, aligned on a microscope stage, and subjected to a pressure-driven flow. In every synthesis cycle, the monomer flow was halted (350 ms) and particles were photopolymerized in the device using UV light filtered through a dichroic filter set (365 nm wavelength light for 100 ns exposure tine). The polymerized particles were then covected into a collection tube for 500 ms. Synthesis occurred at a rate of ~5 particles per second. After synthesis the particles were rinsed. The PEG particles were rinsed 3 times with 1× TET (1×TE with 0.05% (v/v) Tween 20).

Although PEG-DA and PUA were used for the hydrogel microparticles and partial hydrogel microparticles in the examples described herein, any di-acrylated monomers that have been used in stop-flow lithography may be used for the encoded region. Further, any di-acrylated monomers into which UCNs (either nanocrystals with modified surfaces or ligands or nanocrystals with unmodified surfaces or ligands) may be well-dispersed can be employed.

Figure 30:
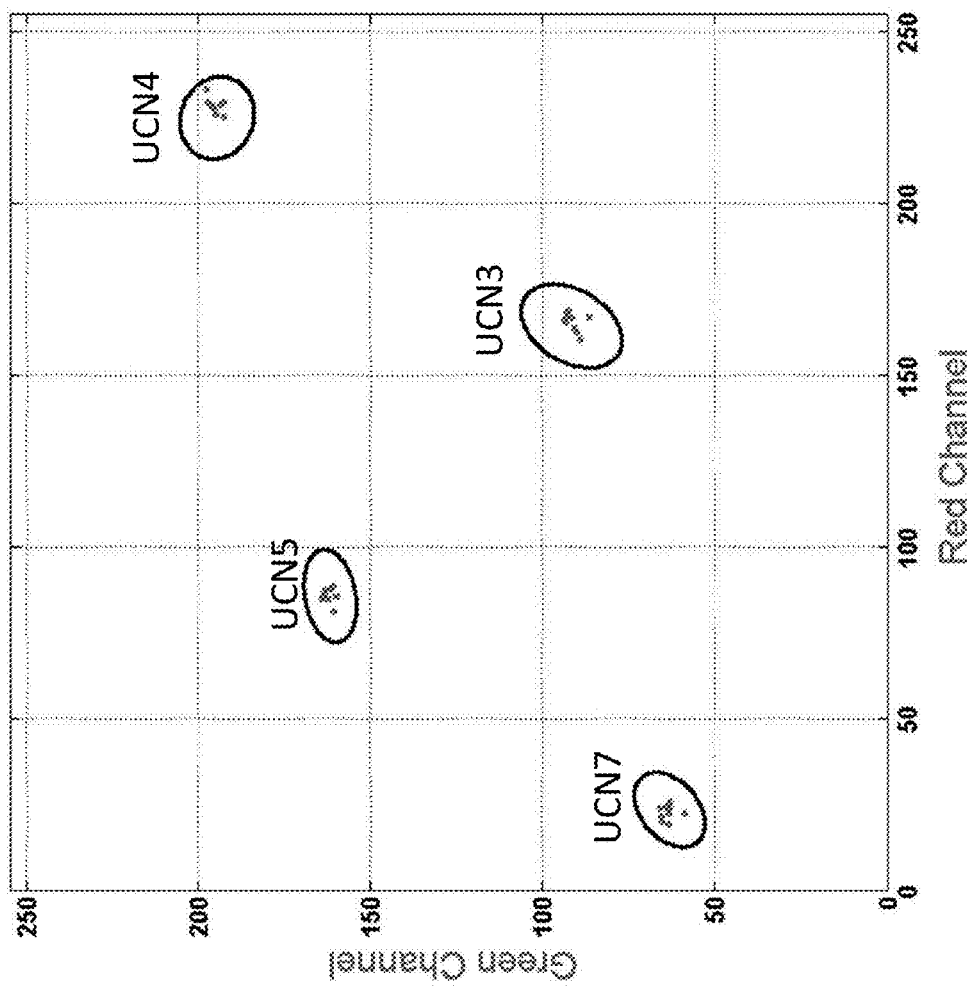
FIG. 30 is a graph of integrated intensity for different color channels for microparticles, in accordance with an embodiment.

In an initial batch of encoded hydrogel microparticles used for testing, each portion of the encoded region included a plurality of nanocrystals selected from the set of types UCN3, UCN4, UCN5 and UCN7, whose characteristics are described above. As used herein, encoded microparticles refers to microparticles that each have one or more portions of the encoded region and that each have one or more types of spectrally distinguishable UCNs. Eight encoded microparticles were illuminated with the NIR diode laser and imaged using a standard CCD image sensor. The integrated intensity was calculated for the red and green channels of the image sensor. FIG. 30 is a plot of the green channel integrated intensity vs. the red channel integrated intensity for each portion of the encoded region in the eight microparticles. As shown, the integrated intensities for the portions of the encoded regions are clumped into groups corresponding to the UCN3, UCN4, UCN5 and UCN7 nanocrystals types. The ellipses are the five-sigma Gaussian fits to the data from the particles having only one type of nanocrystals, which may be considered the "training data." All of the data points for the encoded particles fell within the five-sigma Gaussian fit for the training data.

Figure 31:
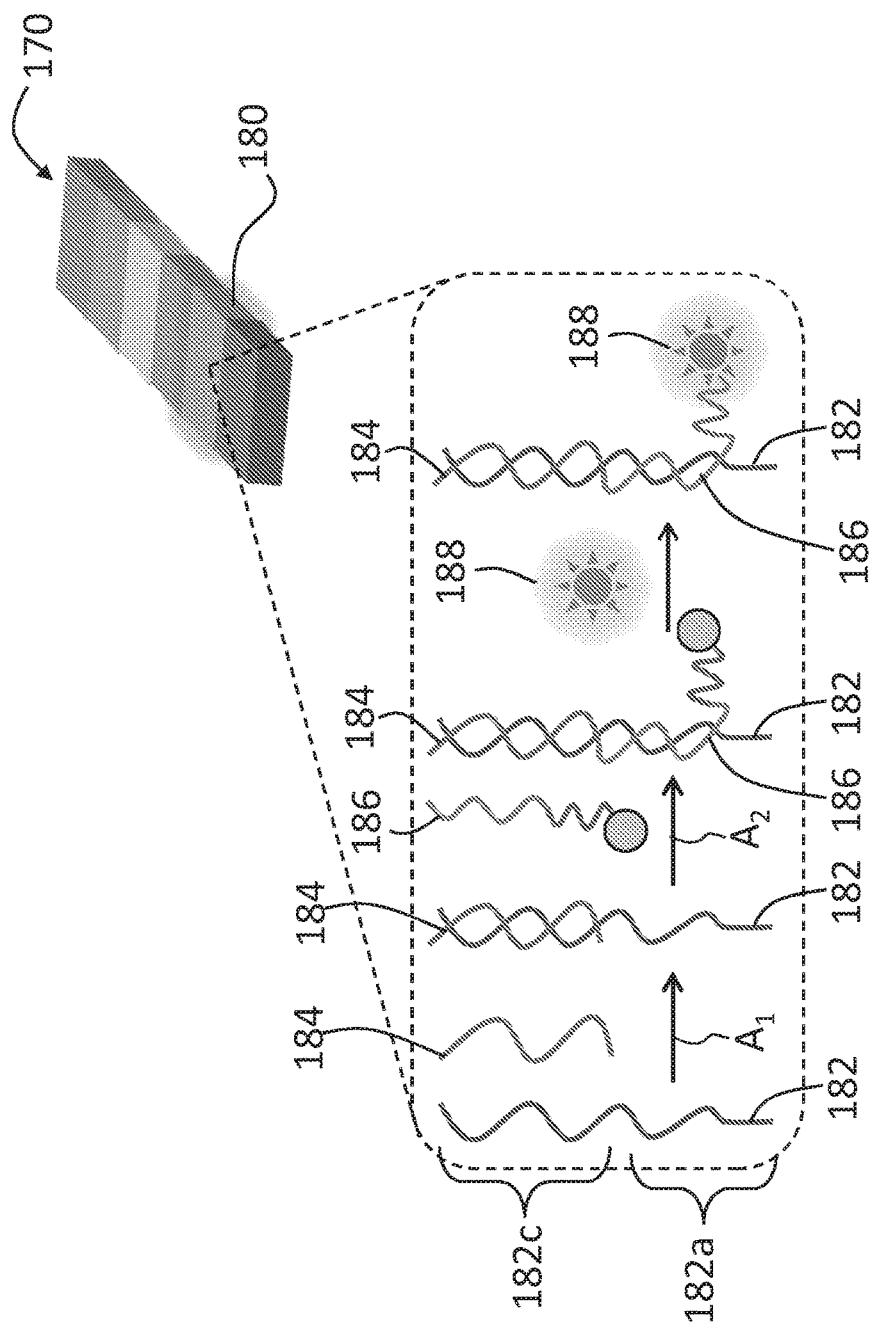
FIG. 31 schematically depicts detection of a nucleic acid of interest by a molecular recognition element in the probe region, in accordance with some embodiments.

FIG. 31 schematically depicts detection of a target nucleic acid of interest by a molecular recognition element, specifically a nucleic acid probe 182, in a probe region 180 of a microparticle 170. In some embodiments, the nucleic acid probe 182 includes a capturing sequence 182c for binding a targeted nucleic acid of interest 184 and an adjacent adapter sequence 182a for binding a universal adaptor. Upon exposure to the target nucleic acid in a sample solution, the target nucleic acid and the capturing sequence hybridize as indicated by arrow A1. After exposure to the sample, the microparticle is exposed to a universal adapter 186 (e.g., a biotinylated universal adapter), which binds to the adapter sequence of the nucleic acid probe and to the hybridized target nucleic acid as indicated by arrow A2. The microparticle is then exposed to a reporter molecule, such as a fluorescence reporter (e.g., streptavidin-phycoerythrin (SA-PE)) that binds to the universal adapter. For a more detailed explanation and other examples of molecular recognition elements and detectable entities that may be employed in the probe region see U.S. Patent Application Publication No. US 2012/0316082 A1, published Dec. 13, 2012, which is incorporated by reference herein in its entirety.

PEG-DA particles with distinct coding and bioassay regions were synthesized, each including an encoding region with five encoding regions (i.e., 5 stripes) yielding an encoding capacity on the order of $10^5$. One set of the synthesized particles contained a microRNA (MiRNA) probe for miR-210 and another contained a probe for mi-R221.

The inventors produced microparticles having two different codes for use in a multiplexed assay. Microparticles with the first code (UCN4, UCN5, UCN3, UCN7, and UCN4 or 45734) included a probe region with a molecular recognition element for 210 miRNA (miR-210). Microparticles with the second code (47534) included a molecular recognition element for 221 miRNA (miR-221). Images of the two encoded microparticles under NIR illumination are shown in FIG. 32.

Figures 33, 34:
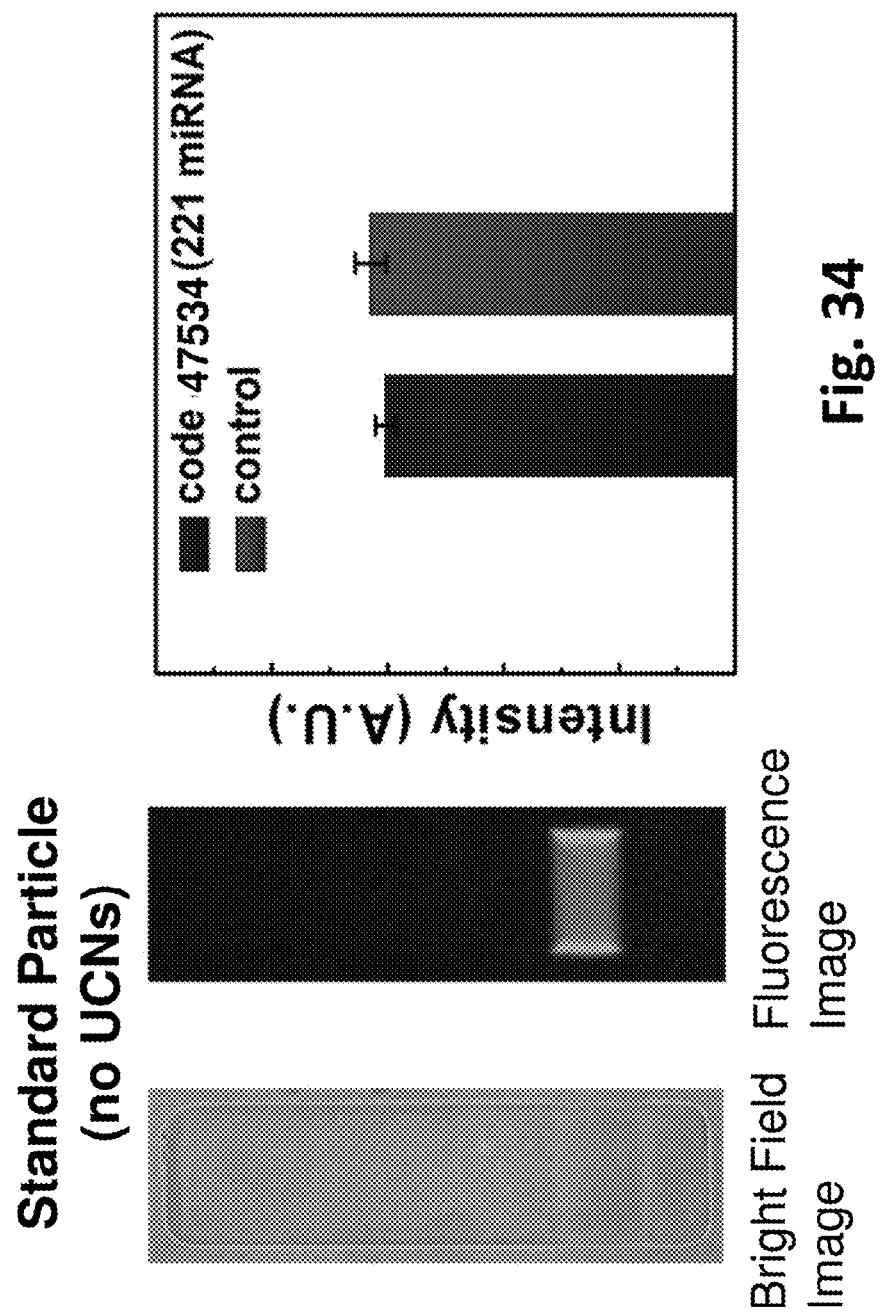
FIG. 33 includes a bright field image and a fluorescence image of a non-encoded standard microparticle, in accordance with an embodiment.
FIG. 34 is a graph of fluorescence intensity for encoded microparticles and for standard (non-encoded) microparticles, in accordance with an embodiment.

In order to compare performance of spectrally-encoded nanoparticle-containing hydrogel microparticles particles to hydrogel particles without UCNs particle, a batch of "standard" hydrogel particles including a miR-221 probe region flanked by two control regions were synthesized. The standard particles had no encoding region and no UCNs. Both the encoded hydrogel microparticles and the standard hydrogel microparticles had probe regions of identical dimensions to ensure similar mass transport and reaction inside the gel network. FIG. 33 shows a bright field image and a fluorescence image of the standard particle with no encoding region and no UCNs after exposure to miR-221. FIG. 34 shows a graph comparing the fluorescence intensity in the probe region for microparticles with the second code exposed to miR-221 and for the control particles exposed to miR-221 including data for six particles of each. As shown by FIG. 34, the fluorescence intensity of the probe region was not affected by the presence of the encoded regions of UCNs.

The spectrally-encoded hydrogel particles functionalized with DNA capture probes for miR-210 and miR-221 were used in a microRNA assay to demonstrate specific and multiplexed detection of the two targets. In the multiplexed assay, microparticles with the two different codes were exposed to four different sample solutions: one containing 500 amol of miR-210, one containing 500 amol of miR-221, one containing 500 amol of both 221 miR-210 and miR-221, and one including neither. This enabled evaluation of encoded microparticles both with regard to standard particles and with regard to specificity. Post-target incubation, bound miRNA targets were labeled using a biotinylated universal linker sequence and a streptavidin-phycoerythrin (SA-PE) fluorophore, and imaged under fluorescence.

Assay reactions were carried out in a final volume of 50 µL inside a 0.65 mL Eppendorf tube. Each reaction contained a total of 75 particles (25 particles of each type: (standard miR-221, spectrally-encoded miR-221, spectrally-encoded miR-210)). Target incubations were carried out in microRNA hybridization buffer for 90 minutes at 55° C. using a thermoshaker (1500 RPM). Post-incubation, particles were rinsed with three 500 µl volumes of microRNA rinse buffer (RB) using centrifugation. After each rinse, supernatant was manually aspirated, leaving 50 µL of solution and particles in the reaction tube. A volume of 235 µL of a ligation mastermix, which was prepared using 100 µL 10×NEB2, 900 µL TET, 800 U/mL T4 DNA ligase, 40 nM biotinylated universal linker sequence, and 250 nM ATP, was then added to the reaction for a 30 minute incubation at 21.5° C. and 1500 RPM. Microparticles were rinsed three more times using microRNA RB and incubated with streptavidin-phycoerythrin at a final concentration of 2 µg/mL for 45 minutes at 21.5° C. and 1500 RPM. After three more rinses with microRNA RB, particles were exchanged into PTET (TET with 25% (v/v) PEG-200) for imaging. DNA sequences for the two probes and the universal linker appear in Table 5 below.

TABLE 5

DNA Sequences

| | Target | Probe Sequence |
|---|---|---|
| SEQ ID No: 1 | miR-210 | 5Acryd/GAT ATA TTT TAT CAG CCG CTG TCA CAC GCA CAG/3InvdT |
| SEQ ID No: 2 | miR-221 | 5Acryd/GAT ATA TTT TAG AAA CCC AGC AGA CAA TGT AGC T/3InvdT |
| SEQ ID No: 3 | Universal Linker | /5Phos/TAAAATATATAAAAAAAAAAAA/3Bio/ |

FIG. 35 shows images of microparticles with the first code and microparticles with the second upon exposure to the four different sample solutions. Fluorescence images and images under NIR illumination (1 W 980 nm NIR diode laser) were captured separately. In the images in FIG. 35, the fluorescence image of each microparticle overlays the image of the microparticle under NIR illumination. As shown, the assay successfully discriminated between the presence of miR-210 and miR-221 in the four sample solutions.

Figure 36:
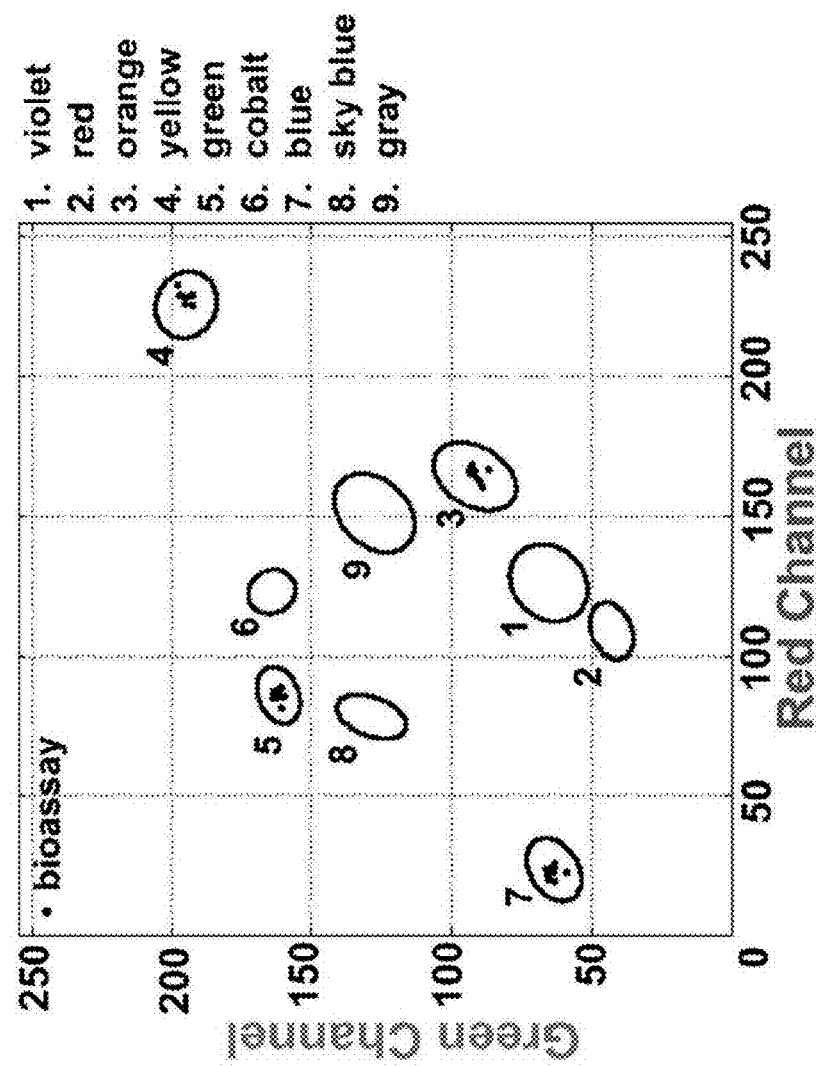
FIG. 36 is a graph of integrated intensity data in red versus green channels for portions or stripes of encoded PEG microparticles.

FIG. 36 is a graph of integrated intensity of each portion of each microparticle for the red and green color channels for the encoded PEG-DA microparticles used for the bioassay. As shown, the encoded PEG-DA microparticle data fits within the five-sigma contours of the training data for all of the encoded PEG-DA microparticles, which means that error rates of less than 1 part per billion (ppb) may be achieved.

Figure 37:
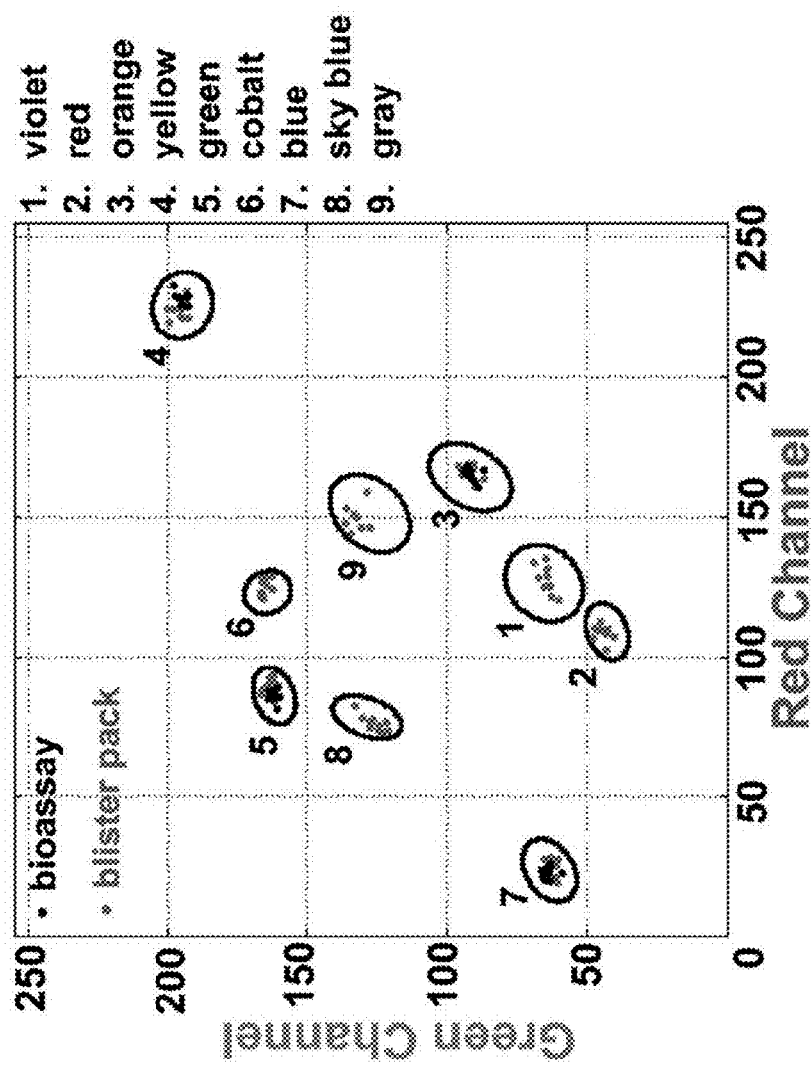
FIG. 37 is a graph of integrated intensity data in red versus green channels for portions or stripes of encoded PUA microparticles and encoded PEG microparticles.

FIG. 37 is a graph of integrated intensity of each portion of each microparticle for the red and green color channels for the PEG-DA microparticles used for the bioassay and for PUA microparticles used for labeling of a blister pack. As shown, the data fits within the five-sigma contours for both types of microparticles. Thus, the reliability of identification of encoded regions applies across different microparticle materials.

The composite images shown in FIG. 35 and the data in FIGS. 34 and 36 demonstrate successful multiplexed miRNA detection, and that the encoding strategy has negligible impact on the fluorescence intensity observed in the probe region, which is an important criterion for quantifying biomolecule concentrations.

Although the microparticles produced included a nucleic acid probe for miRNA as a molecular recognition element, one of ordinary skill in the art would recognize that many different types of molecular recognition elements could be employed and incorporated into the probe region source material of various embodiments. For example, other types of molecular recognition elements that could be employed include, but are not limited to various nucleic acids, miRNA, ssDNA, proteins, receptor proteins, antibodies, enzymes, peptides, aptamer, avimers, Fc domain fragments, phage, carbon nanotube sensors, peptides, etc. Any existing molecular recognition element, biological or not, compatible with the particle synthesis process, may be incorporated.

Although the microparticles produced only included one probe region, in some embodiments, each microparticle may include more than one probe region. For embodiments with more than one probe region, the different probe regions may have different types of molecular recognition elements. In some embodiments, multiple types of molecular recognition elements may be incorporated into one probe region. Although the microparticles produced include a probe region that is distinct from the encoded region, in some embodiments, the probe region may partially or completely overlap with one or more portions of the encoded region.

Example Formation of Hydrogel Microparticles with PEG-DA Probe Region and PUA Encoded Region As noted above, after the inventors selected polyethylene glycol diacrylate PEG-DA as a suitable biocompatible polymer for forming the hydrogel of the probe region, it was discovered that oleic-acid capped UCNs do not disperse in the PEG-DA. Instead the oleic-acid capped UCNs aggregated forming clumped distributions in the PEG-DA pre-polymer solution, which led to clumped distributions of UCNs in the microparticles. Before the inventors developed the method of modifying the oleic acid group to form carboxyl-terminated UCNs, the inventors initially employed a hydrophobic polymer, polyurethane acrylate (PUA) (specifically MINS-300 produced by Minuta Tech, Co. Ltd. of Gyeonggi-Do Korea) for the encoded region in an attempt to address the problem of UCN aggregation. The nanoparticles dispersed well in the MINS-300 hydrophobic PUA, but the MINS-300 hydrophobic PUA wouldn't form a robust cross-linked interface with the PEG-DA of the probe region. The inventors then selected another PUA that is only slightly hydrophilic (specifically MINS-0311 produced by Minuta Tech, Co. Ltd. of Gyeonggi-Do Korea) for the encoded region. The UCNs did not disperse as well in the slightly hydrophilic second PUA MINS-0311; however, the MINS-0311 second PUA formed a robust interface with the PEG-DA of the probe region upon cross-linking. Using the MINS-0311 second PUA as the polymer for the encoded region source materials, the inventors were able to achieve some dispersion of the UCNs in the portions of the encoded region and a robust interface with the PEG-DA probe region.

Figure 38:
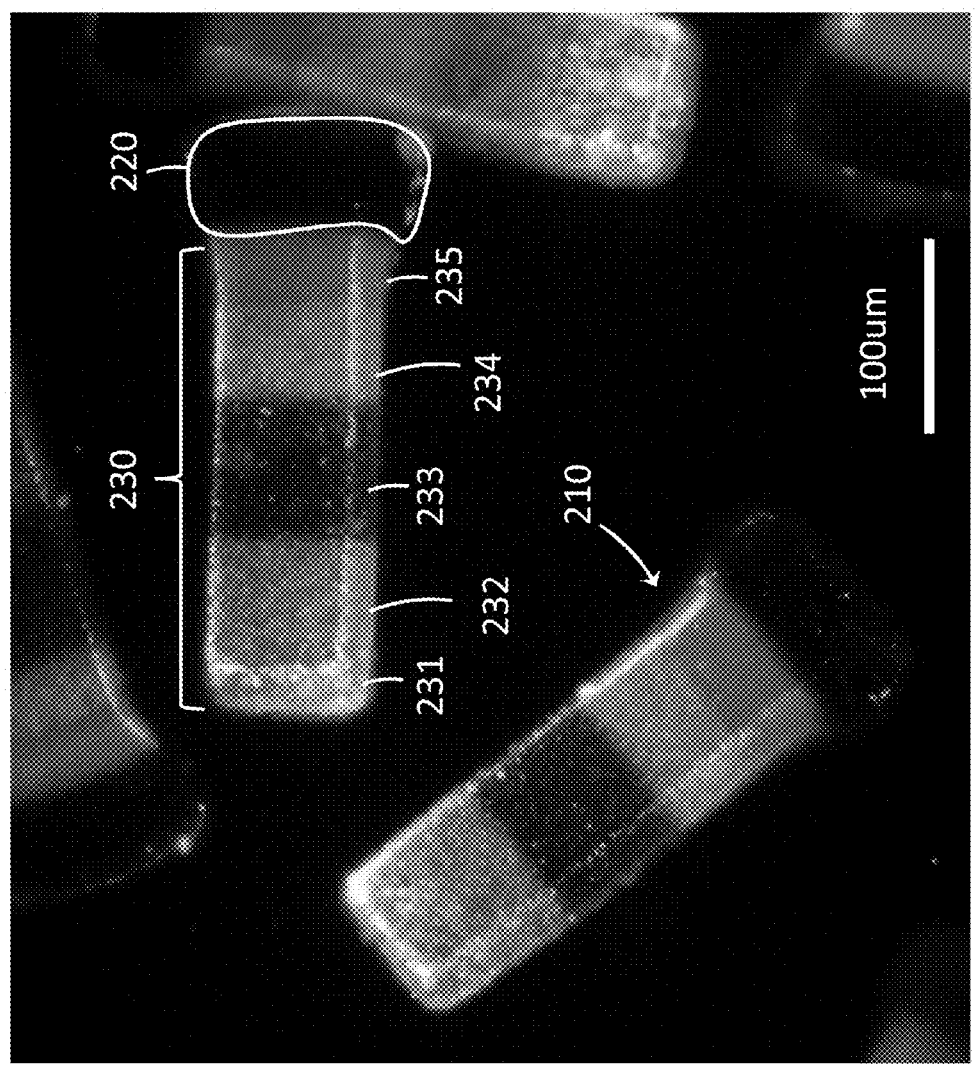
FIG. 38 is an image of microparticles with a PUA encoded region and a PEG-DA probe region under NIR illumination, in accordance with an embodiment.

FIG. 38 is a microscope image of microparticles 210 with a PEG-DA probe region 220 (outlined in white) and a second PUA (specifically, MINS-311) encoded region 230 excited by a NIR light source. Each portion of the encoded region 231, 232, 233, 234, 235 included a plurality of UCN. The presence of color throughout each portion of the encoded region 231-235 indicates that the UCNs were distributed throughout the source materials. However, the nonunifomity of the color in each encoded region 231-235 indicates that the UCNs were not uniformly distributed in the source materials. For comparison, see the images of microparticles in FIG. 26. The microparticles 210 formed with a PEG-DA probe region 220 and a PUA encoded region 230 experienced deformation due to different amounts of swelling in aqueous solvents for the two materials as shown by the white outline of the probe region 220. Despite these shortcomings, the microparticles 210 could still be employed in some bioassay applications. Further, the inventors demonstrated that the UCN could be integrated into a microparticle that has chemically distinct polymers in different portions of the particle.

Any di-acrylated monomers that have been used in stop-flow lithography may be used for the encoded region. Further, any di-acrylated monomers into which UCN (either UCNs with modified surfaces or ligands or UCNs with unmodified surfaces or ligands) may be well-dispersed can be employed.

Figure 39:
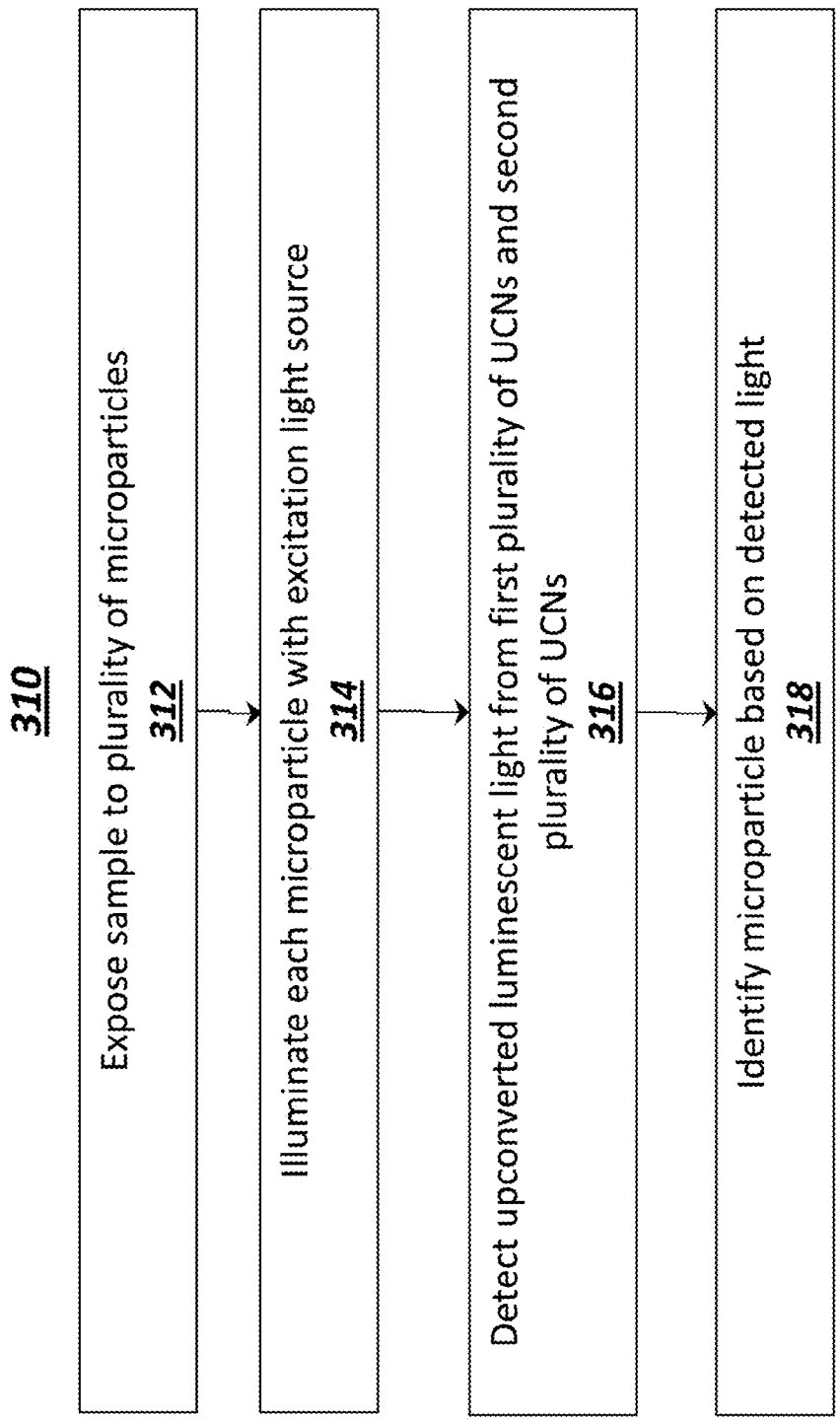
FIG. 39 is a block diagram of a method for performing biochemical or chemical assay, in accordance with an embodiment.

FIG. 39 schematically depicts a method of performing biochemical or chemical assay 310. The method 310 includes exposing a sample to a plurality of microparticles (312). Each microparticle includes a hydrogel or partial-hydrogel body. The body includes a probe region with one or more molecular recognition elements and an encoded region. The body also includes a first plurality of UCN disposed in the first portion of the encoded region and a second plurality of UCN disposed in a second portion of the encoded region spatially separated from the first portion of the encoded region. A spectral signature of the second plurality of UCN is different than a spectral signature of the first plurality of UCN. The method also includes 314 illuminating each microparticle with an excitation light source (e.g., an NIR light source) (314). The method further includes detecting light emitted from the illuminated microparticle (316). The detected light including upconverted luminescent light from the first plurality of UCN and the second plurality of UCN and light associated with the one or more molecular recognition elements. The method also includes identifying each microparticle based on the detected light.

Figure 40:
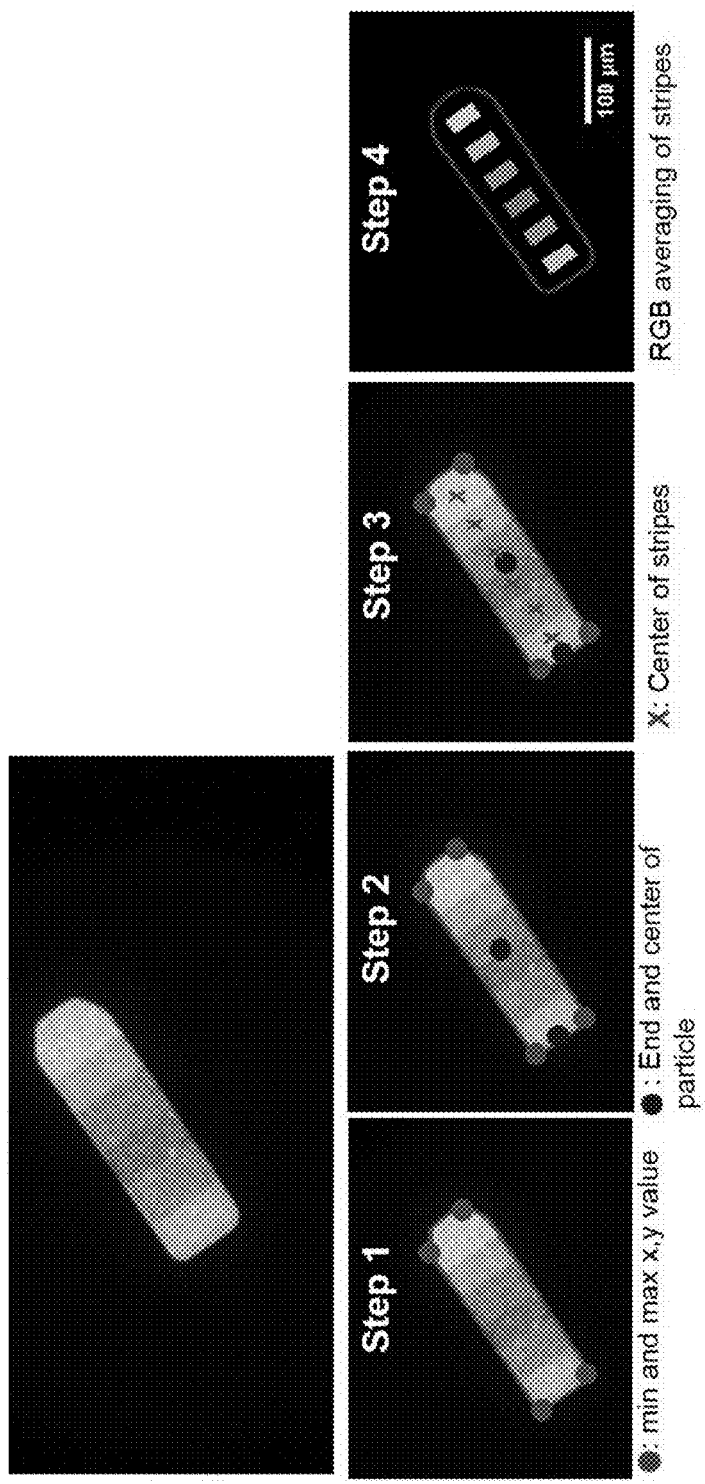
FIG. 40 includes images of a process of reading out spectral codes from a luminescence image of a microparticle, in accordance with some embodiments.
Figure 41:
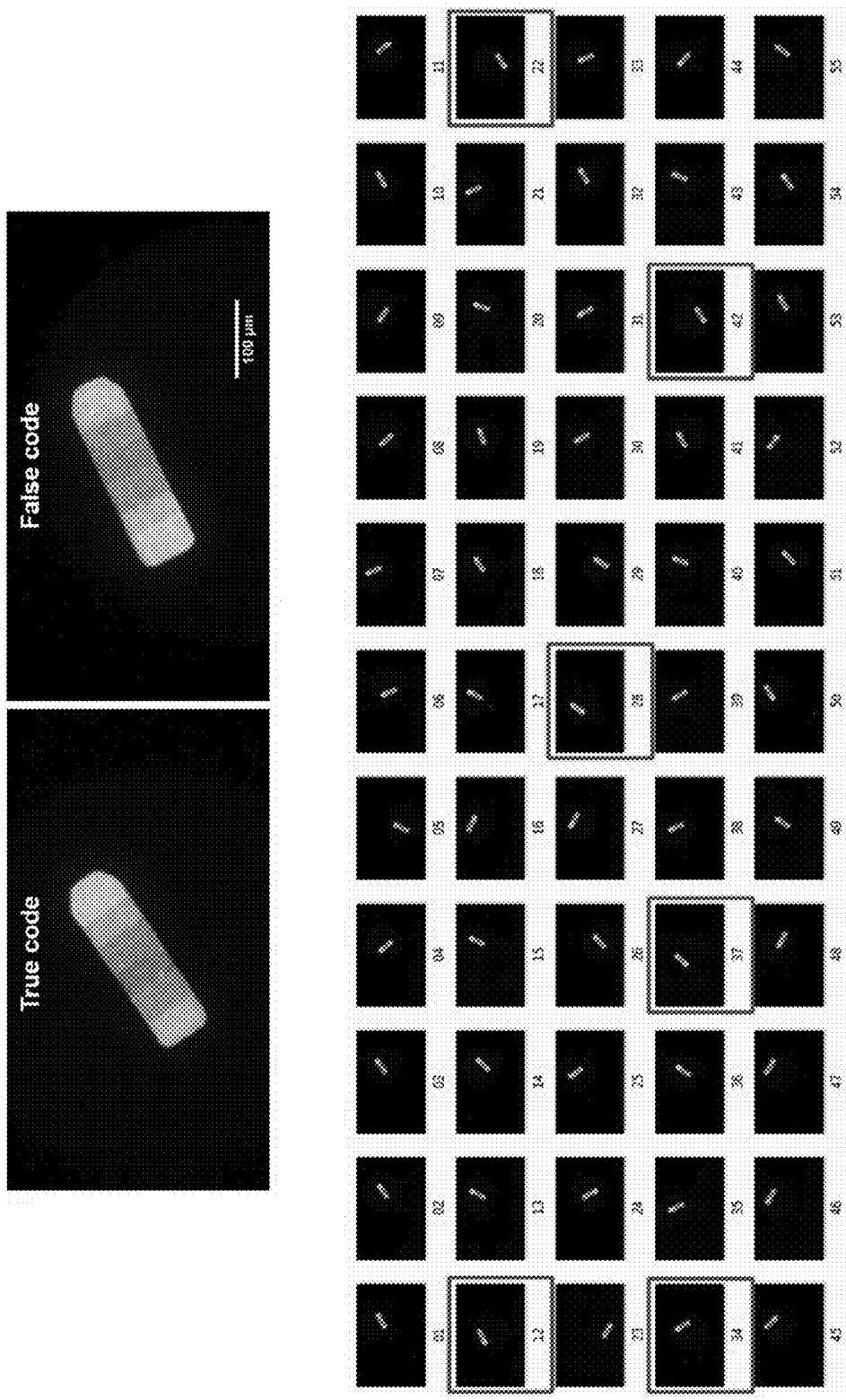
FIG. 41 includes images used to distinguish two different codes of microparticles, in accordance with an embodiment.

A method of reading out the spectral codes of a microparticle is described with respect to FIGS. 40 and 41, which illustrate reading out a microparticle having six encoded regions and no probe region. One of ordinary skill in the art in view of the present disclosure would appreciate how the method may be applied for reading out spectral codes of a microparticle having an encoded region with multiple portions and a probe region. Initially, a maximum or minimum is identified along the x or y axis (step 1). A center and end points of the particle are identified (step 2). A particle orientation is determined and, in the case of an asymmetric particle, a direction of the particle is determined, and the center of each stripe is identified (step 3). An average RGB value is calculated within a sampled area around each stripe (step 4).

Specifically, images of particles with 6 stripes were taken via a CCD decoder and loaded into image processing and analysis software (e.g., MATLAB by Mathworks of Natick, Mass.). Particle boundaries were defined using a grayscale intensity-based edge detection algorithm. Boundary pixel x and y values were averaged to determine the particle centroid. Boundary pixels with minimum and maximum x and y values (four points total) were noted, and distances between adjacent points used to determine the particle end point, or the pixel located on the 2nd shortest edge of the particle boundary and its longitudinal axis. The end pixel and centroid pixel were then used to determine both the code orientation and a director for the particle's longitudinal axis. The centroid of each striped region of the particle was determined by segmenting the particle into six regions (the number of stripes were presumed known a priori) along its longitudinal director. In other embodiments, k-means image segmentation algorithms may be employed to define regions of the particle based on color, without a priori knowledge of the number of particle stripes. RGB values were measured by averaging pixels within each of the six striped regions of particles under test were compared against training RGB values and standard deviations, as determined from a particle training set. If an average set of RGB values fell within 3.5 standard deviations of a training RGB value, the values were determined to match. In this way, 'analog' RGB sequences were translated into 'digital' sequences of spectral signatures.

To test the identification, multiple microparticles were generated with a "true code" and some with a different "false code" as shown in FIG. 41. An automated decoding system employing the process described above with respect to FIG. 40 correctly distinguished the "true code" microparticles that matched a provided "authentic code" from the "false code" microparticles that did not match the provided authentic code, using luminescence images. In FIG. 41, the identified "false code" images are indicated with a box around the image.

Figure 42:
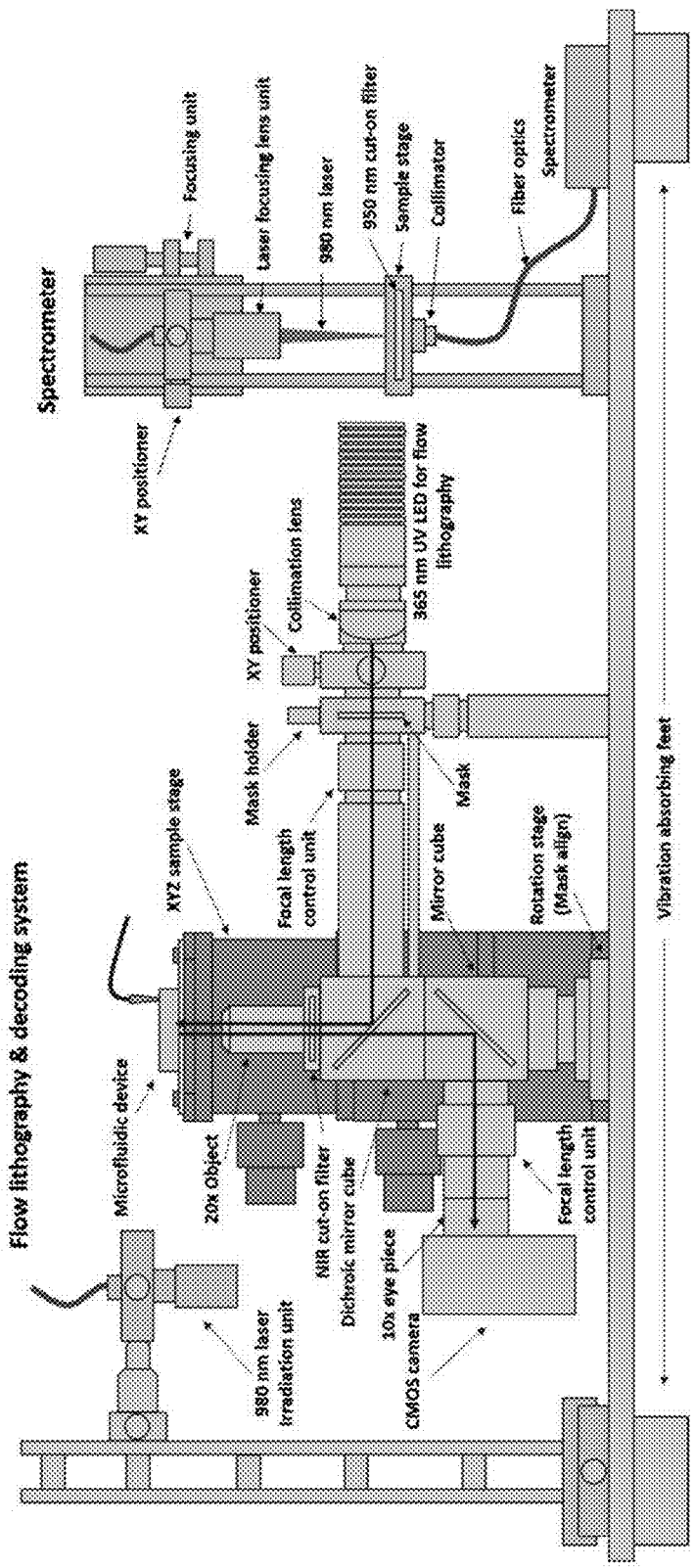
FIG. 42 schematically depicts a flow lithography and decoding system for particle synthesis, in accordance with some embodiments.
Figure 43:
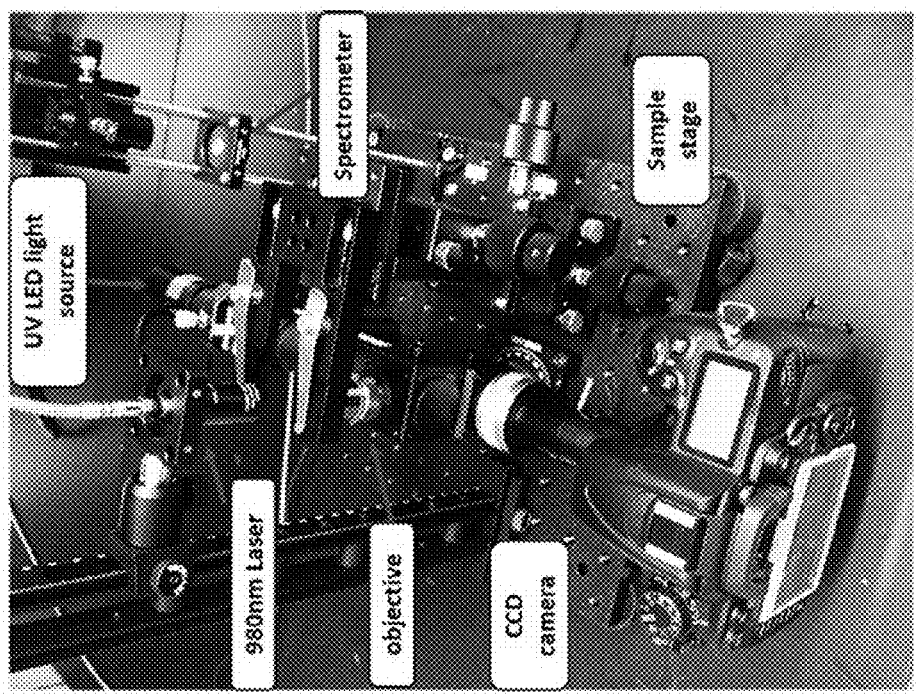
FIG. 43 is an image of the system for particle synthesis of FIG. 42.

Further details regarding an exemplary system of particle synthesis are provided below. FIG. 42 schematically depicts a flow lithography and decoding system for particle synthesis that includes a flow lithography microscope setup, a decoding microscope setup, and a spectrometer setup. FIG. 43 is an image of the flow lithography and decoding system for particle synthesis. The flow lithography microscope setup includes a UV LED light source, a 10× objective (Edmund optics), a CMOS camera, a dichroic cage cube, a dichroic mirror, cage cube-mounted turning prism mirrors, an XYZ sample stage, a mask holder, Ø1" lens tubes, an XY translator, a high-precision zoom housing for Ø1" optics, a 30 mm cage, posts, an LED and valve control relay, which were controlled with instrument control hardware and software, a camera adapter, and a CCD camera. The decoding microscope setup included a 1 W 980 nm laser, a 950 nm cut-on filter, a collimator, a CCD camera adapter, and a CCD camera. The spectrometer setup included a spectrometer, a laser translation stage, an X,Y translating lens mount, NIR achromatic doublet pairs, a collimator, a 950 nm cut-on filter, a 30 mm cage, and posts.

The versatile, high-performance stop-flow lithography (SFL) systems and techniques described herein are a high throughput process for synthesizing particles. In a semicontinuous process, multiple coflowing laminar streams—each containing a single optically active UCN moiety or probe molecule—are convected into a microchannel (e.g., formed from poly(dimethylsiloxane) (PDMS) or a non-swelling thiolene-based resin for use with organic solvents), stopped, and photopolymerized in place via mask-patterned ultraviolet light (365 nm) to form barcoded particles at a rate of 18,000 particles/hr, which are then displaced when flow resumes. This ~$10^4$ particles/hr synthesis rate is by no means limiting; hydrodynamic flow focusing has been used to increase the synthesis rate for similar particles to over $10^5$ particles/hr. The synthesis platform may also be constructed using commercial off-the-shelf parts and free-standing optics. Parallelization in an industrial setting, with no further optimization, could readily increase the facility-scale synthesis throughput by orders of magnitude to meet industrial demand.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

What is claimed:

1. A microparticle for use in a biochemical or chemical assay, the microparticle comprising:
a body comprising a hydrogel, the body including a probe region and an encoded region, the probe region including one or more molecular recognition elements;
a first plurality of upconversion nanocrystals disposed in a first portion of the encoded region, the first plurality of upconversion nanocrystals having a first spectral signature; and
a second plurality of upconversion nanocrystals disposed in a second portion of the encoded region the second plurality of upconversion nanocrystals having a second spectral signature spatially separated from the first portion of the encoded region.

2. The microparticle of claim 1, wherein the second spectral signature is different than the first spectral signature.

3. The microparticle of claim 1, wherein the first plurality of upconversion nanocrystals includes a first material doped with one or more rare earth elements and the second plurality of upconversion nanocrystals includes a second material doped with one or more rare earth elements.

4. The microparticle of claim 1, wherein the body is asymmetric in shape.

5. The microparticle of claim 1, wherein the upconversion nanocrystals are covalently bound to the hydrogel.

6. The microparticle of claim 1, wherein the upconversion nanocrystals are bound to the hydrogel during particle synthesis through an acrylate group.

7. The microparticle of claim 1, wherein for each portion of the encoded region, the plurality of upconversion nanocrystals are dispersed without aggregation.

8. The microparticle of claim 1, further comprising a third plurality of upconversion nanocrystals disposed in a third portion of the encoded region spatially separated from the first portion of the encoded region and spatially separated from the second portion of the encoded region, the third plurality of upconversion nanocrystals having a third spectral signature different from or the same as any one of the first spectral signature or the second spectral signature.

9. The microparticle of claim 8, wherein the encoded region includes at least five different portions.

10. The microparticle of claim 1, wherein each spectral signature includes luminescence in multiple distinct bands within a range of 400-800 nm.

11. The microparticle of claim 1, wherein the probe region comprises polyethylene glycol diacrylate (PEG-DA).

12. The microparticle of claim 1, wherein the encoded region comprises di-acrylated monomer.

13. The microparticle of claim 1, wherein the probe region comprises a first polymer material and the encoding region comprises a second polymer material different than the first polymer material.

14. The microparticle of claim 1, wherein the upconversion nanocrystals are paramagnetic or ferromagnetic.

15. A method of making a hydrogel microparticle for use in a biochemical or chemical assay, the method comprising:
providing a first encoded region source material including a hydrogel and a first plurality of upconversion nanocrystals having a first spectral signature;
providing a second encoded region source material including a hydrogel and a second plurality of upconversion nanocrystals having a second spectral signature;
providing a probe region source material including a hydrogel and one or more molecular recognition elements;
cross-linking the first encoded region source material, the second encoded region source material and the probe region source material forming a first portion of an encoded region, a second portion of the encoded region spatially separated from the first portion, and a probe region with the probe region cross-linked with one or both of the first portion and the second portion of the encoded region to form a contiguous microparticle.

16. The method of claim 15, wherein the second spectral signature is different than the first spectral signature.

17. The method of claim 15, wherein each of the first plurality of upconversion nanocrystals and each of the second plurality of upconversion nanocrystals has a hydrophilic surface.

18. The method of claim 15, wherein the method further comprises providing a third encoded region source material including a hydrogel and a third plurality of upconversion nanocrystals having a third spectral signature different from or the same as any one of the first spectral signature or the second spectral signature, and wherein the third encoded region source material forms a third portion of the encoded region of the microparticle spatially separated from the first portion of the encoded region and the second portion of the encoded region.

19. The method of claim 18, wherein the method further comprises providing a fourth encoded region source material including a hydrogel and a fourth plurality of upconversion nanocrystals having a fourth spectral signature different from or the same as any one of the first spectral signature, the second spectral signature, or the third spectral signature, and wherein the fourth encoded region source material forms a fourth portion of the encoded region of the microparticle spatially separated from the first portion of the encoded region, the second portion of the encoded region, and the third portion of the encoded region.

20. The method of claim 15, further comprising selecting the first plurality of upconversion nanocrystals and the second plurality of upconversion nanocrystals by comparing an expected first spectral response with an expected second spectral response, wherein the expected first spectral response is a convolution of an emission spectrum of the first plurality of upconversion nanocrystals and a spectral response of an image sensor, and wherein the expected second spectral response is a convolution of an emission spectrum of the second plurality of upconversion nanocrystals and a spectral response of an image sensor.

21. The method of claim 15, wherein providing the first encoded region source material comprises forming the first plurality of upconversion nanocrystals.

22. The method of claim 15, wherein providing the first encoded region source material comprises modifying a surface of each of the first plurality of upconversion nanocrystals.

23. The method of claim 15, wherein the upconversion nanocrystals are paramagnetic or ferromagnetic.

24. A method of performing a biochemical or chemical assay comprising:
 exposing a sample to a plurality of microparticles, each microparticle comprising:
  a body comprising a hydrogel, the body including a probe region with one or more molecular recognition elements to detect a target of interest in the sample and an encoded region;
  a first plurality of upconversion nanocrystals disposed in a first portion of the encoded region, the first plurality of upconversion nanocrystals having a first spectral signature; and
  a second plurality of upconversion nanocrystals disposed in a second portion of the encoded region spatially separated from the first portion of the encoded region, the second plurality of upconversion nanocrystals having a second spectral signature different than the first spectral signature;
 for each microparticle, illuminating the microparticle with an excitation light source;
 for each microparticle, detecting light emitted from the illuminated microparticle, the detected light including upconverted luminescent light from the first plurality of upconversion nanocrystals and the second plurality of upconversion nanocrystals and light associated with detection of the target of interest in the sample by the one or more molecular recognition elements; and
 identifying each microparticle based on the detected light.

25. The method of claim 24, wherein multiple of the plurality of microparticles are illuminated with an excitation light source simultaneously.

26. The method of claim 24, wherein light is detected from multiple of the plurality of microparticles simultaneously.

27. The method of claim 24, wherein, for each microparticle, detecting light emitted from the illuminated microparticle includes detecting the first spectral signature emitted by the first portion of the encoded region and detecting the second spectral signature emitted by the second portion of the encoded region.

28. The method of claim 24, wherein the upconversion nanocrystals are paramagnetic.

* * * * *

SEQUENCE LISTING

<160> NUMBER OF SEQ ID NOS: 3

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' Acrydite
<220> FEATURE:
<221> NAME/KEY: modified_base
<222> LOCATION: (34)..(34)
<223> OTHER INFORMATION: 3' Inverted dT

<400> SEQUENCE: 1
gatatatttt atcagccgct gtcacacgca cagt                                 34

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' Acrydite
<220> FEATURE:
<221> NAME/KEY: modified_base
<222> LOCATION: (35)..(35)
<223> OTHER INFORMATION: 3' Inverted dT

<400> SEQUENCE: 2
gatatatttt agaaacccag cagacaatgt agctt                                35

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<220> FEATURE:
<223> OTHER INFORMATION: 5' Phosphate
<220> FEATURE:
<223> OTHER INFORMATION: 3' Biotin

<400> SEQUENCE: 3
taaaatatat aaaaaaaaaa aa                                                    22
```